(12) United States Patent
Coulthard et al.

(10) Patent No.: US 11,957,829 B2
(45) Date of Patent: Apr. 16, 2024

(54) SYSTEM AND METHOD FOR IMPROVING BATTERY LIFE OF PORTABLE NEGATIVE-PRESSURE THERAPY THROUGH HYSTERESIS CONTROL

(71) Applicant: KCI Licensing, Inc., San Antonio, TX (US)

(72) Inventors: Richard Daniel John Coulthard, Verwood (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 17/991,528

(22) Filed: Nov. 21, 2022

(65) Prior Publication Data

US 2023/0093695 A1 Mar. 23, 2023

Related U.S. Application Data

(63) Continuation of application No. 16/484,635, filed as application No. PCT/US2018/017351 on Feb. 8, 2018, now abandoned.
(Continued)

(51) Int. Cl.
*A61M 1/00* (2006.01)

(52) U.S. Cl.
CPC ................ *A61M 1/73* (2021.05); *A61M 1/74* (2021.05); *A61M 1/75* (2021.05); *A61M 1/96* (2021.05);
(Continued)

(58) Field of Classification Search
CPC ............ A61M 1/73; A61M 1/74; A61M 1/75; A61M 1/90; A61M 1/96; A61M 2205/3334; A61M 2205/3344; A61M 2205/8212
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/US2018/017351, dated Jul. 9, 2018.
(Continued)

*Primary Examiner* — Jessica Arble

(57) ABSTRACT

A system comprises a negative-pressure source including a pump and an electric motor for maintaining negative-pressure at the wound and a pressure sensor for sensing a wound site pressure (WP). The system further comprises a system controller coupled to the first pressure sensor and the electric motor. The system controller maintains the wound site pressure (WP) within a hysteresis band by the application of power to the electric motor from a battery power source, based upon, at least in part a flow rate (FR) of fluid between the pump and the wound site as determined by the system controller. The hysteresis band including a maximum wound site pressure (WPMax) and a minimum wound site pressure (WPMin).

40 Claims, 10 Drawing Sheets

Related U.S. Application Data

(60) Provisional application No. 62/467,683, filed on Mar. 6, 2017.

(52) U.S. Cl.
CPC ............ *A61M 2205/3334* (2013.01); *A61M 2205/3344* (2013.01); *A61M 2205/8212* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |
| 2015/0133829 A1* | 5/2015 | DeBusk ............ A61F 13/00068 601/6 |
| 2015/0165182 A1* | 6/2015 | Pratt .................... A61M 37/00 604/290 |
| 2016/0136339 A1* | 5/2016 | Begin .................... A61M 1/98 604/319 |
| 2016/0184496 A1* | 6/2016 | Jaecklein ................ A61M 1/78 604/318 |
| 2018/0264181 A1* | 9/2018 | Gregory .................. A61M 1/98 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| EP | 0358302 | A2 | 3/1990 | | |
|---|---|---|---|---|---|
| EP | 1018967 | A1 | 7/2000 | | |
| GB | 692578 | A | 6/1953 | | |
| GB | 2195255 | A | 4/1988 | | |
| GB | 2 197 789 | A | 6/1988 | | |
| GB | 2 220 357 | A | 1/1990 | | |
| GB | 2 235 877 | A | 3/1991 | | |
| GB | 2 329 127 | A | 3/1999 | | |
| GB | 2 333 965 | A | 8/1999 | | |
| JP | 4129536 | B2 | 8/2008 | | |
| SG | 71559 | | 4/2002 | | |
| WO | 80/02182 | A1 | 10/1980 | | |
| WO | 87/04626 | A1 | 8/1987 | | |
| WO | 90/010424 | A1 | 9/1990 | | |
| WO | 93/009727 | A1 | 5/1993 | | |
| WO | 94/20041 | A1 | 9/1994 | | |
| WO | 96/05873 | A1 | 2/1996 | | |
| WO | 97/18007 | A1 | 5/1997 | | |
| WO | 99/13793 | A1 | 3/1999 | | |
| WO | 2013064852 | A1 | 5/2013 | | |
| WO | WO-2013064852 | A1 * | 5/2013 | .......... | A61M 1/0031 |
| WO | 2017027850 | A1 | 2/2017 | | |
| WO | WO-2017027850 | A1 * | 2/2017 | ............ | A61F 13/00 |
| WO | 2017079174 | A1 | 5/2017 | | |
| WO | 2017160412 | A1 | 9/2017 | | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

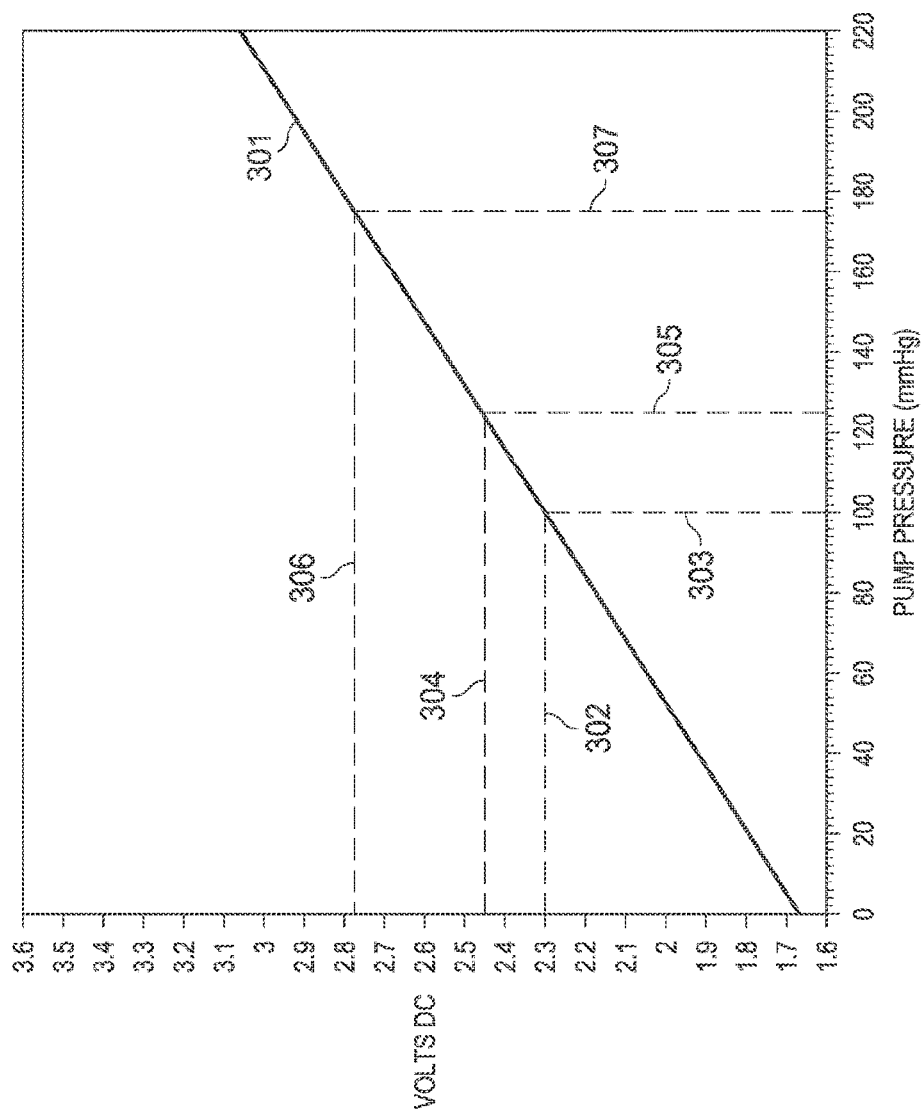

SYSTEM AND METHOD FOR IMPROVING BATTERY LIFE OF PORTABLE NEGATIVE-PRESSURE THERAPY THROUGH HYSTERESIS CONTROL

RELATED APPLICATIONS

This application is a continuation of U.S. patent application Ser. No. 16/484,635, filed Aug. 8, 2019, which is a U.S. National Stage Entry of PCT/US2018/017351, filed Feb. 8, 2018, which claims the benefit, under 35 USC § 119(e), of the filing of U.S. Provisional Patent Application Ser. No. 62/467,683, entitled "System And Method For Improving Battery Life Of Portable Negative-Pressure Therapy Through Hysteresis Control," filed Mar. 6, 2017, which are incorporated herein by reference for all purposes.

TECHNICAL FIELD

The present invention relates generally to systems and methods for improving the battery life of battery-powered devices through hysteresis control. Such battery-powered devices include, without limitation, negative-pressure wound therapy systems.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds where the system is configured to remove fluid and infectious material from the wound site. Regardless of the etiology of a wound, whether trauma, surgery, or another cause, proper care of the wound site is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure wound therapy are widely known, the provision of negative-pressure wound therapy over a therapeutic life cycle, which can be 7 days or more, is increasingly being performed with small portable disposable therapy devices that are powered by batteries rather than a connection to an electrical outlet. Since, these small portable therapy devices are often disposable and typically use non-rechargeable batteries to avoid adding cost to a disposable unit or a burden to a user by requiring the batteries to be periodically charged, the design of these devices is challenging. Because the limiting factor in many applications is not the ability of their pumps to run harder in the case of a therapeutic dressing with an imperfect seal, but the limited capacity of their batteries under these conditions.

An alternative is therefore needed to either requiring the user to obtain a better seal during dressing application, requiring a new dressing that better accommodates the user and is therefore easier to obtain a seal with, requiring the device to have higher capacity batteries or the user to change or re-charge the batteries, is needed. What is needed is a system level approach to reduce the power consumption over the therapeutic life cycle, at a reasonable cost that does not unduly burden to the user.

BRIEF SUMMARY

While the present invention can be used to improve the battery life of battery-powered devices generally, the description and examples herein primarily focus on negative-pressure wound therapy systems. It is understood by those skilled in the art that the description and examples herein are not intended to limit the present invention to negative-pressure wound therapy devices only.

New and useful systems, apparatuses, and methods for maintaining negative-pressure in low and high leak conditions in a negative-pressure therapy environment are disclosed herein. Illustrative embodiments are also provided to enable a person skilled in the art to make and use the claimed subject matter.

The reduced pressure provided by a reduced pressure treatment system to a tissue site such as, for example, an incision or a wound may need to be properly controlled to increase the effectiveness of the reduced pressure treatment. The reduced pressure treatment system may include a pump for providing reduced pressure, a wound dressing disposed adjacent the wound, and a drape that covers both to provide a sealed environment for providing the reduced pressure treatment from the pump to the sealed environment. Leaks and blockages may occur in the components of the reduced pressure treatment system such as, for example, leaks between the drape and the tissue site, that may need to be detected in order to adjust the pressure provided by the pump to maintain effective treatment.

The type of method used for controlling reduced pressure treatment systems, i.e., the wound site pressure control band, may vary depending on the magnitude of the pressure leaks or blockages and/or the rate of change of the pressure leaks or blockages. Consequently, the wound site pressure control band best suited for a high leak rate may be different from the wound site pressure control band best suited for a low leak rate. For example, a system controller and control methods are described herein that include both a narrow hysteresis control band and a wide hysteresis control band and an algorithm for switching between the two based on the level of leakage of components in the negative-pressure treatment system. The system controller and control methods may select the wide hysteresis control band for high leakage conditions to conserve battery power and reduce noise from the pump. More specifically, the system controller may include a bang-bang controller and the bang-bang controller might operate more frequently to maintain the narrow hysteresis control band in a high leakage condition which would reduce battery power and expose the patient to frequent humming of the pump, while the electric motor controller might operate less frequently to maintain the wide hysteresis control band which would conserve battery power and be less irritating to the patient because it would not need to be on as frequently.

In one embodiment, a system comprises a negative-pressure source including a pump and an electric motor for maintaining negative-pressure at a wound site and a pressure sensor for sensing a wound site pressure (WP). The system may further comprise a system controller coupled to the first pressure sensor and the electric motor. The system controller may maintain the wound site pressure (WP) within a hysteresis band by the application of power to the electric motor from a battery power source, based upon, at least in part, a flow rate (FR) of fluid between the pump and the wound site as determined by the system controller. The hysteresis band may include a maximum wound site pressure (WPMax) and a minimum wound site pressure (WPMin).

In another example embodiment, a system for stimulating healing of tissue at a wound site comprises a manifold configured to be positioned at a wound site and adapted to be covered by a drape to form a seal around the wound site for maintaining negative-pressure at the wound site. The system may further include a negative-pressure source and the negative-pressure source may include a pump and an electric motor for driving the pump in response to an application of power from a power source, and the pump may be adapted to generate a pump pressure (PP) and may be adapted to be fluidly coupled to the porous pad for the application of negative-pressure to the wound site. The system may further include a first pressure sensor and the pressure sensor may have an input for sensing a wound site pressure (WP) and an output for providing a wound site pressure signal indicative of the wound site pressure (WP). The system may further include a system controller electrically coupled to the output of the first pressure sensor and the electric motor to control the wound site pressure (WP) at the wound site, the system controller may further include a bang-bang controller and the bang-bang controller may be configured to compare the wound site pressure (WP) to a hysteresis control band and may maintain the wound site pressure (WP) within the hysteresis control band. The hysteresis control band may further include a maximum wound site pressure ($WP_{Max}$) and a minimum wound site pressure ($WP_{Min}$), and the maximum wound site pressure ($WP_{Max}$) and a minimum wound site pressure ($WP_{Min}$) may be based upon, at least in part, a flow rate (FR) of fluid between the pump and the porous pad, which may be determined by the system controller.

One or more of the following features may be included. The system may also be a portable system powered by a primary cell battery and the primary cell may be a non-rechargeable lithium battery; alternatively the portable system may be powered by a secondary cell battery and the secondary cell may be a rechargeable lithium-ion battery. The pump may be a diaphragm pump and the electric motor may be a Direct Current (DC) motor and the power applied to the DC motor may be varied by varying a voltage applied to the DC motor or a current drawn by the DC motor. The system controller may be configured to determine a flow rate (FR) by a time rate of change of the voltage applied to or the current drawn by the DC motor, and further configured to select a narrow hysteresis control band when the flow rate (FR) is less than a first target flow rate (TFR1), indicating a low-leak condition in the system, and a wide hysteresis control band when the flow rate (FR) is greater than a second target flow rate (TFR2), indicating a high-leak condition in the system. The first target flow rate (TFR1) may be less than the second target flow rate (TFR2) or substantially equal to the second target flow rate (TFR2). The system controller may be configured to determine the battery charge level (BCL) and further configured to select a wide hysteresis control band if the battery charge level (BCL) is less than a first target battery charge level (TCL1), indicating a low battery charge level in the system, and a narrow hysteresis control band if the battery charge level (BCL) is greater than a second target battery charge level (TCL2), indicating a high battery charge level in the system. The first target battery charge level (TCL1) may be less than the second target battery charge level (TCL2) or substantially equal to the second target battery charge level (TCL2). The bang-bang controller may reduce negative-pressure at the wound site by reducing the power applied to the DC motor when the wound site pressure (WP) is greater than the maximum wound site pressure ($WP_{Max}$) and may increase negative-pressure at the wound site by increasing the power applied to the DC motor when the wound site pressure (WP) is less than the minimum wound site pressure ($WP_{Min}$). The system may also include a second pressure sensor and the pressure sensor may have an input for sensing a pump pressure (PP) and an output providing a pump pressure signal to the system controller indicative of the pump pressure (PP).

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 2 is a graph illustrating stall voltage characteristics for a pump motor that may be used in the reduced pressure therapy system of FIG. 1 wherein the x-axis represents the vacuum pressure loading for the pump motor and the y-axis represents the stall voltage;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
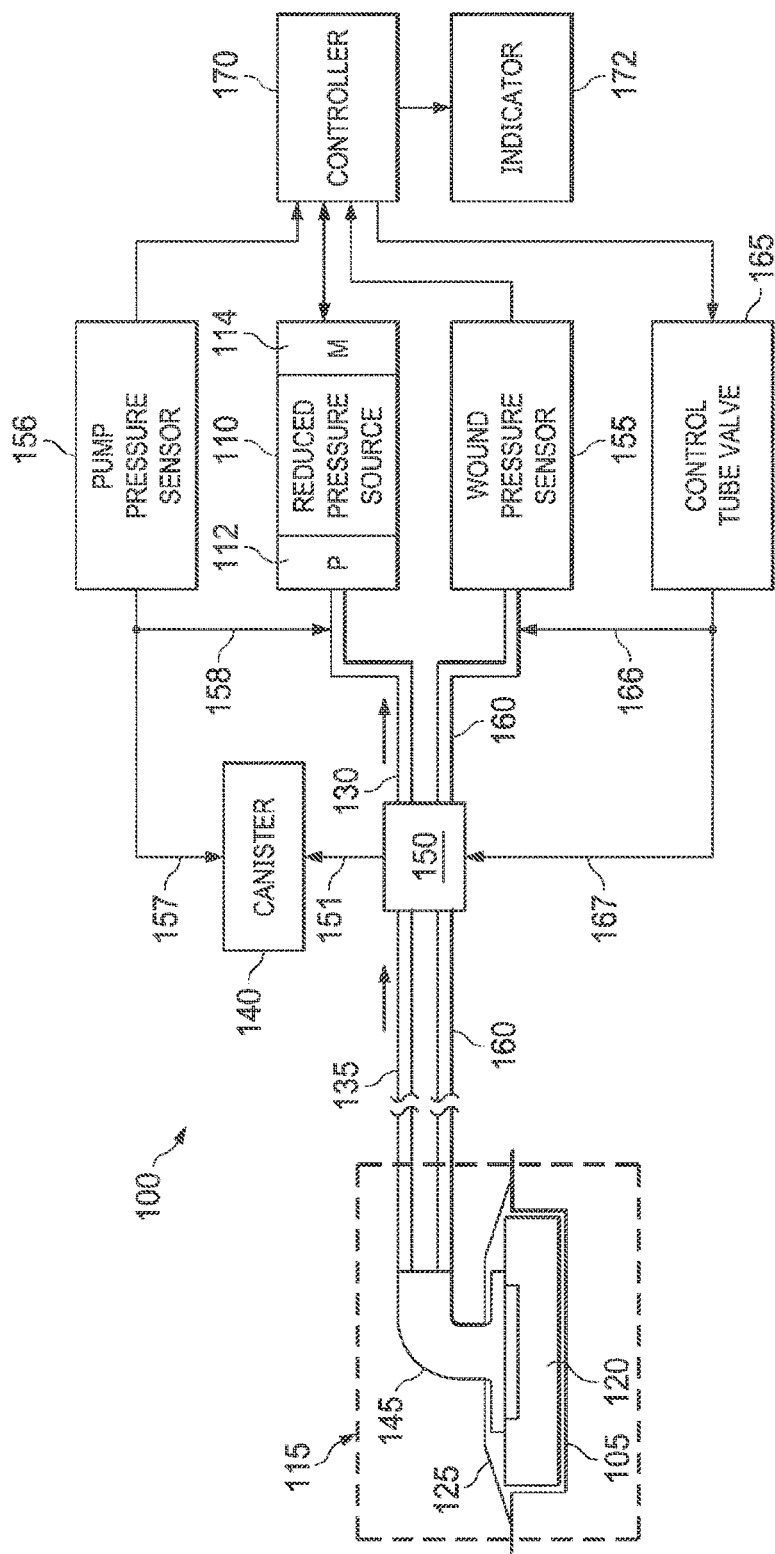
FIG. 1 is a functional block diagram of an embodiment of one example of a reduced-pressure therapy system including a system controller coupled to a pump motor and a pump that can provide hybrid control of pressure being provided to a tissue site in accordance with this specification.

FIG. 1 is a simplified functional block diagram of an example embodiment of a reduced-pressure therapy system 100 that can provide negative-pressure therapy in accordance with this specification. More specifically, the therapy system 100 may be used for controlling which pump pressure hysteresis control band is utilized to provide the appropriate amount of reduced pressure to tissue site 105. Tissue site 105 may be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 may include a wound, diseased tissue, or defective tissue, the tissue site may further include healthy tissue that is not wounded, diseased, or defective. The application of reduced pressure to tissue site 105 may be used to promote the drainage of exudate and other liquids from tissue site 105, as well as promote the growth of additional tissue. In the case in which tissue site 105 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

The reduced pressure applied to the tissue site 105 may be provided by a reduced pressure source 110. Reduced pressure source 110 may be any type of manually, mechanically, or electrically operated pump. Non-limiting examples of reduced pressure source 110 include devices that are driven by stored energy, and which are capable of producing a reduced pressure. Examples of these stored energy, reduced pressure sources include, without limitation, pumps driven by primary and secondary cells, piezoelectric energy, spring energy, solar energy, kinetic energy, energy stored in capacitors, combustion, and energy developed by Sterling or similar cycles. Still other devices and processes that may be used or included in reduced pressure source 110 include syringes, lead screws, ratchets, clockwork-driven devices, pendulum-driven devices, manual generators, osmotic processes, thermal heating processes, and processes in which vacuum pressures are generated by condensation. In another embodiment, reduced pressure source 110 may include a pressure pump 112 wherein the pressure pump 112 provides negative or reduced pressure, i.e., a pump pressure (PP), to the tissue site 105 that may be driven by a DC motor 114 electrically coupled to a system controller 170 which is also a component of the reduced-pressure therapy system 100, also referred to as a system controller. Preferably, the pressure pump 112 uses low amounts of power and is capable of operating for an extended period of time on a single charge of a battery (not shown) such as, for example, a diaphragm pump 112. The electric motor 114 may be a direct-current motor powered by a DC power supply such as, for example, the battery.

In some embodiments, the provision of negative-pressure wound therapy over a therapeutic life cycle, which may be 7-day (168-hour) or more therapeutic life cycle, may be performed by a small portable therapy device 100 powered by a primary cell battery, which may be a non-rechargeable lithium battery. The small portable therapy device 100 may further be disposable and may use a primary non-rechargeable battery to avoid adding cost to a disposable unit or inconveniencing the user by requiring the battery to be periodically charge the battery during the therapeutic life cycle. The small portable therapy device 100 may also be powered by a plurality of batteries. For example, the small portable therapy device 100 may be powered by 3 AA sized batteries. Alternatively the small portable therapy device 100 may be powered by a secondary cell battery, which may be a rechargeable lithium-ion battery pack or a rechargeable lithium polymer battery pack, wherein the period of time between subsequent recharges of the battery may be increased as a result of the system and methods disclosed herein. The small portable device may further be configured with integrated inductive coil, which may facilitate wireless charging of the secondary cell battery of the small portable therapy device 100 while being worn, during periods of patient rest, or both.

In one example embodiment, the reduced pressure source 110 comprises a DC motor 114 powered by the battery, i.e., the applied power. The applied power may be varied to control the speed of the DC motor 114 by varying either the current or the voltage applied to the DC motor 114, i.e., the "applied voltage" (VA). The applied voltage (VA) may be varied, for example, by modulating the voltage with a square wave and varying the duty cycle of the square wave to control the speed of the DC motor 114. The reduced pressure source 110 also comprises a pressure pump 112 that provides a reduced pressure or vacuum to the tissue site 105. Consequently, the pressure pump 112 represents the load on the DC motor 114 so that when the therapy requires that the reduced pressure at the tissue site 105 needs to be increased, the applied voltage (VA) provided to the DC motor 114 is increased to achieve the targeted reduced pressure at the tissue site 105. One skilled in the art knows that the DC motor 114 will not run or turn the pump until the applied voltage (VA) is sufficient to overcome the inertia or load of the pressure pump 112, which in this case may be a diaphragm pump 112.

Referring more specifically to FIG. 2, a graph 301 illustrating the voltages for the DC motor 114 necessary to start the pressure pump 112 is shown wherein the X-axis represents the pump pressure (PP) loading the DC pump motor and the Y-axis represents the applied voltage (VA). For example, the system controller 170 may need to apply at least 2.3V to the DC motor 114 before it will turn the pressure pump 112 when loaded at a pressure of 100 mmHg as indicated by the dashed lines 302, 303. Applying any less than 2.3V to the DC motor 114 would yield insufficient power for the DC motor 114 to turn the pressure pump 112, i.e., the loaded motor would remain stopped or "stalled" so that the DC motor 114 is unable to turn the pressure pump 112. Hence, the 2.3V value is often referred to in the industry as the "stall voltage" that would be calculated for a DC motor 114 under a load of 100 mmHg of pressure, i.e., the "stall pressure." Correspondingly, the system controller 170 may need to apply a larger voltage of at least 2.45V 304 to the DC motor 114 before it will turn the pressure pump 112 when loaded at a greater pressure of 125 mmHg 305. Applying any less than the stall voltage of 2.45V to the DC motor 114 would not be sufficient to cause the DC motor 114 to turn the pressure pump 112 under a stall pressure of 125 mmHg Variations in the stall voltage are proportional to the variations in the pressure load on the DC motor 114, i.e., the greater the pressure load is on the DC motor 114, the greater the stall voltage needed to overcome the pressure load.

The specific stall voltage for a specific DC motor 114 used to drive a diaphragm pump 112 can typically be determined by one skilled in the art from the specifications available for the DC motor 114. The diaphragm pump and DC motor 114 may be an integrated device such as, for example, a Thomas Model No. 30130002 series 4.5V diaphragm pump 112 for which such information is readily available. (Thomas; thomas.de@gardnerdenver.com) Referring again to FIG. 2, the graph 301 illustrating the stall voltage for the pump motor, the Y-axis represents the stall voltages calculated for this Thomas motor based on the specifications presently available at the Thomas website referred to above. The examples provided in the paragraph above include voltages and pressures that are exemplary only. The graph 301 simply illustrates that one skilled in the art can calculate the various stall voltages for a DC motor 114 based on specifications typically available for that motor. Those working with miniature diaphragm pumps 112 that are driven by a DC motor 114, such as the Thomas DC motor 114, often refer to the stall voltage as the "stall power", i.e., the product of the stall voltage and the rated current of the specific DC motor 114.

Data from pump specifications is typically limited to the relation of maximum flow to vacuum pressure at maximum pump voltage (e.g., 4.5V for Thomas pump identified above). Positive pressures are specified in mbar units (mmHg of positive pressure=0.7500616827042* mbars) and vacuum pressures are specified in terms of percent vacuum. For example, if 100% maximum vacuum is specified at 760 mmHg, 40% maximum vacuum would be equal to 304 mmHg (=0.4*760 mmHg). In this example, the 304 mmHg of vacuum pressure would be the theoretical maximum vacuum pressure that we could attain if the pump was run at 4.5V and allowed to run until it the DC motor 114 stalls. The graph 301 in FIG. 2 was generated based on the DC motor specifications and the stall voltages observed that were needed to drive this pump.

The equation for calculating the stall voltage for this particular pump is as follows: Stall Voltage=1.638V+ (0.006515V/mmHg*XmmHg), where X is the current vacuum pressure. Therefore, at 50 mmHg of vacuum, the stall voltage equals 1.96V (1.638+(0.006515*50)); at 125 mmHg of vacuum, the stall voltage equals 2.45V (1.638+ (0.006515*125)) as indicated by the dashed lines 304, 305; and at 175 mmHg of vacuum, the stall voltage equals 2.78V (1.638+(0.006515*175)) as indicated by the dashed lines 306, 307. Again, the higher the vacuum pressure, the higher the applied voltage that is needed to start the pump. Otherwise, the pump stalls and will not move until the necessary stall will voltage is applied. When the pump stalls, the DC motor 114 simply overheats which can damage the DC motor 114 and reduce battery life.

In some embodiments, the diaphragm pump 112 may be designed to pump liquids, slurries, sludge or a combination thereof. There are many advantages to using a diaphragm pump 112 in a negative-pressure wound therapy device. For example, diaphragm pumps may be designed to handle liquids with different viscosities and even liquids that contain a considerable amount of solid material. Diaphragm pumps may further be manufactured from almost any material which makes them suitable for medical applications and are self-priming However, despite the many advantages of using a diaphragm pump in a negative-pressure wound therapy device they do have some limitations in terms of their operating efficiency. For example, like many electrical devices, particularly many types of electric motor, diaphragm pumps are subject to an inrush current, which may be significantly higher than the steady state value. This inrush current or switch-on surge current is the maximum, instantaneous current drawn by an electrical device when it if first turned on, and may persist at this level for a couple of cycles in the case of a motor before dropping back to the steady state value. For example, in the case of the diaphragm pump 112 the current drawn may drop by 60% or more from its initial peak inrush value to its steady state value. Furthermore, the physical components of the pneumatic section of the diaphragm pump 112 may also have an initial static friction associated with them that has to be overcome at startup. For at least these reasons the diaphragm pump 112 may need to complete a number of cycles before it starts to effectively perform.

Figure 2A:
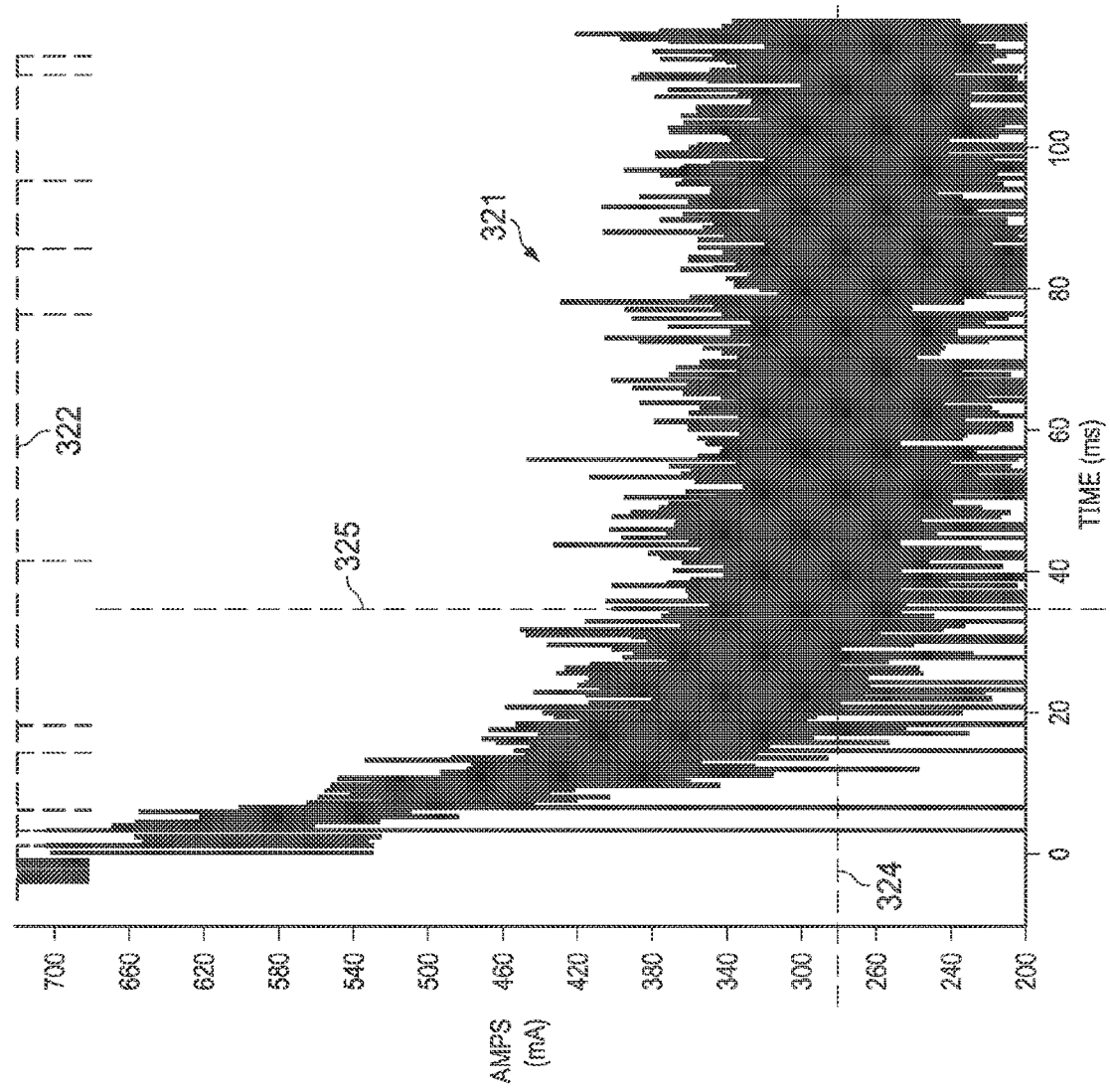
FIG. 2A is a graph illustrating surge current characteristics for a pump motor that may be used in the reduced pressure therapy system of FIG. 1 wherein the y-axis represents the surge current and the x-axis represents time in milliseconds (ms).

Referring more specifically to FIG. 2A, a graph 321 illustrating the currents necessary to start the DC motor 114/diaphragm pump 112, combination at startup is shown wherein the X-axis represents time in milliseconds (ms) and the Y-axis represents the current drawn in milliamps (mA). For example, the current drawn by the DC motor 114 may initially peak at about 715 mA at startup (0 ms) in order to turn the diaphragm pump 112 when operating at a nominal voltage of 3V as indicated by the line 322. The current drawn by the DC motor 114 may then fall to a steady-state value of about 275 mA after 35 ms as indicated by the lines 324 and 325. As disclosed herein there may be an existing static pressure load on the DC motor 114 in the system and the diaphragm pump 112 will have to work harder to overcome this and the static frictional demands disclosed above. For example, the system may be loaded with an existing pressure load of 100 mmHg at startup. Using these values in an illustrative example it may be determined that:

The additional energy used during the first 35 ms=0.023J (1) Or 438 mA×0.5×3V×35 ms The approximate energy used in the first 35 ms=0.052J (2) Or 0.23J+277 mA×3V×35 ms The energy used in a steady state one second period=0.831J (3) Or 277 mA×3V×1S The total energy used during a one second pulse=0.854J (4) Or 0.831J+0.023J The total energy used during a half second pulse=0.438J (5) Or 0.415J+0.023J Referring again to (4) and (5) it can be seen that the additional energy used during the first 35 ms (0.023J) as a result of the inrush current may become increasingly significant as the pulse duration is and fully OFF for 9 seconds, and repeat, to maintain an average target pressure of 125 mmHg at the wound site, wherein the total energy used during the one second pulse may be 0.854J. In this instance the pressure at the wound site may cycle within a relatively wide tolerance band. Alternately the system controller 170 may be configured to maintain the average target pressure by turning the pump 112 fully ON for 100 ms in every 1 second period, wherein the total energy used during a comparable 10 second period would be 1.060J or 0.831J+0.023J×10. In this instance the pressure at the wound site may cycle within a relatively small tolerance band but a significant percentage (21%) of the power feed will be allocated to these start-up inefficiencies rather than maintaining the average target pressure and this will adversely affect the battery capacity required to achieve the therapeutic life cycle. As an illustrative example, in testing a simple system that used a pressure switch and a simple electronic circuit to control a pump showed an increase of battery life of 16% when switching from a narrow hysteresis control band (2 mmHg span) to a wide hysteresis control band (10 mmHg span).

We will further see in the bang-bang control system disclosed below that a bang-bang control system with narrow limits will require a proportionally greater number of starts than a bang-bang control system with wider limits and will therefore incur more of the inefficiencies associated with start-ups while maintaining a target pressure (TP). The controller system may utilize this characteristic, for example, in some instances it may be preferable to compete the therapeutic life cycle with a relatively wide tolerance band rather than attempt to maintain a narrow tolerance band and fail to do so because the batteries have insufficient capacity to do so. In some instances the system may also be configured to returned to the narrow hysteresis control band once it has determined that the batteries have been recharged/replaced or the leak is have been addressed.

Referring back to FIG. 1, the reduced pressure source 110 may provide reduced pressure to the tissue site 105 via a dressing 115. Dressing 115 may include a tissue interface such as, for example, a manifold 120 which may be placed adjacent to or in contact with the tissue site 105. Manifold 120 may be a biocompatible, porous material that is capable of being placed in contact with tissue site 105 and distributing reduced pressure to the tissue site 105. Manifold 120 may be made from foam, gauze, felted mat, or any other material suited to a particular biological application. Manifold 120 may include a plurality of flow channels or pathways to facilitate distribution of reduced pressure or fluids to or from tissue site 105.

In one embodiment, manifold 120 is a porous foam and includes a plurality of interconnected cells or pores that act as flow channels. The porous foam may be a polyurethane, open-cell, reticulated foam such as GranuFoam manufactured by Kinetic Concepts, Inc. of San Antonio, Texas If an open-cell foam is used, the porosity may vary, but is preferably about 400 to 600 microns. The flow channels allow fluid communication throughout the portion of manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through manifold 120. The manifold 120 may further include portions that include "closed cells." These closed-cells portions of manifold 120 contain a plurality of cells, the majority of which are not fluidly connected to adjacent cells. Closed-cell portions may be selectively disposed in manifold 120 to prevent transmission of fluids through perimeter surfaces of manifold 120.

Manifold 120 may also be constructed from bioresorbable materials that do not have to be removed from a patient's body following use of reduced pressure therapy system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 120 may further serve as a scaffold for new cell-growth, or a scaffold material may be used in conjunction with manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-friction (i.e., a high content of air).

The dressing 115 may also include sealing member 125 also referred to as a drape or cover. Manifold 120 may be secured to tissue site 105 using sealing member 125. Sealing member 125 may be a cover that is used to secure manifold 120 at tissue site 105. While sealing member 125 may be impermeable or semi-permeable, in one example sealing member 125 is capable of maintaining a reduced pressure at tissue site 105 after installation of the sealing member 125 over manifold 120. Sealing member 125 may be a flexible drape or film made from a silicone based compound, acrylic, hydrogel or hydrogel-foaming material, or any other biocompatible material that includes the impermeability or permeability characteristics desired for tissue site 105. Sealing member 125 may be formed of a hydrophobic material to prevent moisture absorption by the sealing member 125. In one embodiment, sealing member 125 is configured to provide a sealed connection with the tissue surrounding manifold 120 and tissue site 105. The sealed connection may be provided by an adhesive (not shown) positioned along a perimeter of sealing member 125 or on any portion of sealing member 125 to secure sealing member 125 to the manifold 120 or the undamaged epidermis peripheral to a tissue site, i.e., the peritissue. The adhesive may be pre-positioned on sealing member 125 or may be sprayed or otherwise applied to sealing member 125 immediately prior to installing sealing member 125.

In general, components of the therapy system 100 may be coupled directly or indirectly. Components may be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts The reduced pressure generated by reduced pressure source 110 may be applied to tissue site 105 through source tube 130 and delivery tube 135. Source tube 130 and delivery tube 135 may be any tube through which a gas, liquid, gel, or other fluid may flow. For example, exudate from tissue site 105 may flow through delivery tube 135. In FIG. 1, source tube 130 couples reduced pressure source 110 to a canister 140 and delivery tube 135 couples the canister 140 to the dressing 115. However, in another embodiment, reduced pressure source 135 may be directly coupled to dressing 115 using delivery tube 135.

Source tube 130 and delivery tube 135 may be made from any material. Source tube 130 and delivery tube 135 may be either flexible or inflexible. Also, source tube 130 and delivery tube 135 may include one or more paths or lumens through which fluid may flow. For example, delivery tube 135 may include two lumens. In this example, one lumen may be used for the passage of exudate from tissue site 105 to canister 140. The other lumen may be used to deliver fluids, such as air, antibacterial agents, antiviral agents, cell-growth promotion agents, irrigation fluids, or other chemically active agents, to tissue site 105. The fluid source from which these fluids originate is not shown in FIG. 1. Additional details regarding the inclusion of multi-lumen tubes in reduced pressure therapy system 100 are provided below.

In one embodiment, delivery tube 135 is coupled to manifold 120 via connection member 145. Connection member 145 permits the passage of fluid from manifold 120 to delivery tube 135, and vice versa. For example, exudates collected from tissue site 105 using manifold 120 may enter delivery tube 135 via connection member 145. In another embodiment, reduced pressure therapy system 100 does not include connection member 145. In this embodiment, delivery tube 135 may be inserted directly into sealing member 125 or manifold 120 such that an end of delivery tube 135 is adjacent to or in contact with manifold 120.

Liquid, such as exudate, from tissue site 105 may flow through delivery tube 135 into canister 140. Canister 140 may be any device or cavity capable of containing a fluid, such as gases and liquids, as well as fluids that contain solids. For example, canister 140 may contain exudates from tissue site 105. Source tube 130 and delivery tube 135 may be directly connected to canister 140, or may be coupled to canister 140 via a connector, such as connector 150, as indicated by arrow 151. The canister 140 may be a flexible or rigid canister, a bag, or pouch fluidly connected to manifold 120 by delivery tube 135. Canister 140 may be a separate canister or may be operably combined with reduced pressure source 110 to collect exudate and fluids.

Reduced pressure therapy system 100 may further comprise a first pressure sensor 155 electrically coupled to the system controller 170. First pressure sensor 155 detects an actual reduced pressure at or proximate the tissue site 105, i.e., the tissue site pressure or wound site pressure (WP). The reference to the word "wound" as part of the term wound site pressure (WP) is exemplary only and does not limit the term or description herein as applying to the measurement of pressure at other types of tissue sites such as, for example, incisions or subcutaneous cavities. In one non-limiting example, first pressure sensor 155 is a silicon piezo-resistive gauge pressure sensor. First pressure sensor 155 may be configured to detect the wound site pressure (WP) via a control tube 160 fluidly coupled to the connection member 145 or via one of the lumens of the delivery to 135 as described above through the connector 150. Control tube 160 is any tube through which a gas may flow. Control tube 160 may be made from any material. Control tube 160 may be either flexible or inflexible. Also, control tube 160 may include one or more paths or lumens through which fluid may flow.

Reduced pressure therapy system 100 may further comprise a second pressure sensor 156 electrically coupled to the system controller 170. Second pressure sensor 156 detects a reduced pressure at or downstream from the canister 140 indicated by arrows 157 and 158, respectively, i.e., the pump pressure (PP). In one non-limiting example, second pressure sensor 156 is a silicon piezo-resistive gauge pressure sensor. The second pressure sensor 156 may be fluidly coupled directly to the canister 144 or the source tube 130, or indirectly via a control tube (not shown) as indicated by the arrows 157 and 158, to detect the pump pressure (PP). The second pressure sensor 156 may also be fluidly coupled to the canister 144 through the connector 150.

In FIG. 1, control tube 160 is shown as passing through connector 150. However, the placement of control tube 160 may be varied to accommodate particular needs and applications. For example, control tube 160 may be routed through canister 140, along an outside surface of canister 140, or may bypass canister 140. The end of control tube 160 that is opposite of first pressure sensor 155 may be coupled to manifold 120 via the connection member 145. In another example, control tube 160 may be inserted directly into sealing member 125 or manifold 120 such that an end of control tube 160 is adjacent to or in contact with manifold 120.

Figure 1A:
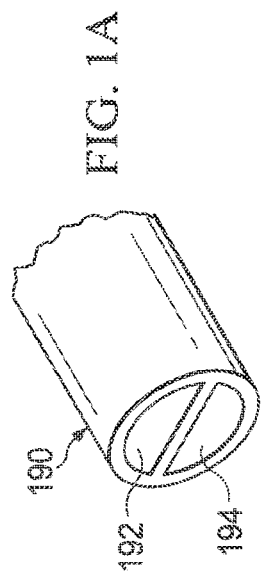
FIG. 1A is a perspective view of a multi-lumen tube that may be used in the reduced pressure therapy system of FIG. 1 in accordance with an illustrative embodiment of the invention.

In another embodiment, delivery tube 135 and control tube 160 are each lumens in a single multi-lumen tube. Source tube 130 and control tube 160 may also each be lumens in a single multi-lumen tube. In the example in which reduced pressure source 110 is coupled to manifold 120 using only delivery tube 135, a single multi-lumen tube may be used to couple both reduced pressure source 110 and first pressure sensor 155 to manifold 120. Turning to FIG. 1A, a perspective view of a multi-lumen tube is depicted in accordance with an illustrative embodiment of the present invention. Specifically, FIG. 1A depicts multi-lumen tube 190, which may be implemented in a reduced pressure treatment system, such as reduced pressure therapy system 100 in FIG. 1.

Multi-lumen tube 190 includes two lumens. Specifically, multi-lumen tube 190 includes lumens 192 and 194. Although multi-lumen tube 190 includes two lumens 192 and 194, multi-lumen tube may have any number of lumens, such as three, four, or ten. In one embodiment, one of lumens 192 and 194, such as lumen 192, is a delivery tube or source tube, such as delivery tube 135 and source tube 130 in FIG. 1. In another embodiment, one of lumens 192 and 194, such as lumen 194, is a control tube, such as control tube 160 in FIG. 1. By incorporating a combination of a delivery tube, source tube, and control tube as lumens in a single multi-lumen tube, the number of separate tubes included in the reduced pressure treatment system may be reduced. The reduced number of tubes simplifies the reduced pressure treatment system for use by a user, and lessens the burden of carrying the reduced pressure treatment system.

In some embodiments, pressure sensors 155 and 156 may be located anywhere on or within the reduced pressure therapy system 100, for example, they may be wireless sensors. Referring back to FIG. 1, first pressure sensor 155 is shown to be remote from tissue site 105. In this example, the reduced pressure at tissue site 105 may be detected from remotely located first pressure sensor 155 through the control tube 160, which permits the flow of gas. Also in this example, second pressure sensor 156 may be directly or indirectly coupled to other remotely located components of reduced pressure therapy system 100, such as reduced pressure source 110, the canister 140, or any other illustrated component of reduced pressure therapy system 100. In another example, first pressure sensor 155 may not require the use of control tube 160 to detect the pressure at tissue site 105. In one non-limiting example, first pressure sensor 155 is directly coupled to manifold 120 or placed between sealing member 125 and manifold 120.

Reduced pressure therapy system 100 may also include control tube valve 165. Control tube valve 165 may be coupled to control tube 160 as indicated by arrow 166 or indirectly coupled to the source tube 134 or the canister 140 as indicated by arrow 168. Control tube valve 165 may be any valve capable of relieving the reduced pressure in control tube 160. Non-limiting examples of control tube valve 165 include a pneumatic solenoid valve, a proportional valve, or a mechanical valve. In one example, control tube valve 165 may be manually controlled by a caregiver. In another example, control tube valve 165 may be controlled by the system controller 170. In one embodiment, control tube valve 165 may be opened to relieve the reduced pressure in control tube 160 or the source tube 130 when a blockage is detected in either one. Such a blockage may occur, for example, when exudate or other fluid from tissue site 105 clogs control tube 160 or the source tube 130. By relieving the reduced pressure in control tube 160 or the source tube 130 via control tube valve 165, the blockage may be cleared from either one.

In operation, the manifold 120 may be placed within, over, on, or otherwise proximate to a tissue site. The sealing member 125 may be placed over the manifold 120 and sealed to tissue near the tissue site 105. For example, the sealing member 125 may be sealed to undamaged epidermis peripheral to a tissue site, i.e., the peritissue. Thus, the dressing 115 can provide a sealed therapeutic environment proximate to a tissue site, substantially isolated from the external environment, and the reduced pressure source 110 can reduce the pressure in the sealed therapeutic environment. Reduced pressure applied across the tissue site through the manifold 120 in the sealed therapeutic environment can induce macrostrain and microstrain in the tissue site, as well as remove exudates and other fluids from the tissue site, which can be collected in the canister 140 and disposed of properly.

The fluid mechanics of using a reduced-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative-pressure, for example.

In general, exudates and other fluids flow toward lower pressure along a fluid path. Thus, the term "downstream" typically implies something in a fluid path relatively closer to a reduced-pressure source, and conversely, the term "upstream" implies something relatively further away from a negative-pressure source. Similarly, it may be convenient to describe certain features in terms of fluid "inlet" or "outlet" in such a frame of reference. This orientation is generally presumed for purposes of describing various features and components of reduced-pressure therapy systems herein. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative-pressure may be used in certain tissue areas to grow additional tissue that may be harvested and transplanted to another tissue location.

The term "negative or reduced pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative-pressure typically refer to a decrease in absolute pressure, while decreases in negative-pressure typically refer to an increase in absolute pressure.

A negative-pressure source, such as the reduced pressure source 110, may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as processing units, alarm indicators, memory, databases, software, display devices, or user interfaces that further facilitate negative-pressure therapy. For example, the reduced pressure source 110 and the system controller 170 may be housed within a therapy control unit. While the amount and nature of negative-pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

As indicated above, the applied voltage (VA) provided to the DC motor 114 is used to control the pump pressure (PP) and ultimately achieve the desired or targeted pressure at the tissue site 105. Correspondingly, the applied voltage (VA) provides an indication of the pump pressure (PP) and may be monitored by the system controller 170 which in turn may determine the time rate of change of the applied voltage (VA) that necessarily corresponds to the time rate of change of the pump pressure (PP). The controller 170 may use this computation for determining the flow rate of air between the reduced pressure source 110 and tissue site 105, i.e., the flow rate (FR). In another embodiment, the reduced pressure therapy system 100 may further comprise a sensing device (not shown) that directly measures the flow rate (FR) such as, for example, a flow-meter or a differential processor for computing the time rate of change in the difference between the wound site pressure (WP) and the pump pressure (PP). The flow rate (FR) may be measured, for example, as cubic centimeters of air per minute (cc/min), between the reduced pressure source 110 and the tissue site 105. The flow rate (FR) provides some indication of the extent to which the dressing 115 or other components of the negative-pressure system 100 might be leaking to reduce the pressure at the tissue site 105 below the desired pressure targeted for therapy. For example, a high flow rate (FR) might indicate that the dressing 115 or other components of the therapy system 100 are considered to be in a "high leakage condition," while a lower flow rate (FR) might indicate that the dressing 115 or other components of the therapy system 100 are considered to be in a more efficient "low leakage condition" requiring less battery power for driving the DC motor 114 to continue running in order to offset the lower leakage.

The controller 170 may be an integrated or separate component of the reduced-pressure treatment system 100. Controller 170 may be any device capable of processing data, such as data from first pressure sensor 155 and/or the second pressure sensor 156. Controller 170 may also control the operation of one or more components of reduced pressure therapy system 100, such as reduced pressure source 110, DC motor 114, control tube valve 165, pressure sensors 155 and 156, and an indicator 172. The controller 170 may control and receive data from other components (not shown) of the reduced pressure source 110 including the pressure pump 112 and the DC motor 114. In one embodiment, controller 170 receives and processes data, such as the wound site pressure (WP) from the first pressure sensor 155, the pump pressure (PP) from the second pressure sensor 156, and the flow rate (FR) from monitoring the applied voltage (VA) to the DC motor 114 as described above. The controller 170 may also control the operation of one or more components of reduced pressure therapy system 100 to manage the wound site pressure (WP) at tissue site 105. In one embodiment, controller 170 may including an input for receiving a desired target pressure (TP) set by a clinician or other user and may be program for processing data relating to the setting and inputting of the target pressure (TP) to be applied to the tissue site 105.

In one example embodiment, the target pressure (TP) may be a fixed pressure value determined by a user/caregiver as the reduced pressure target desired for therapy at the tissue site 105 and then provided as input to the system controller 170. The user may be a nurse or a doctor or other approved clinician who prescribes the desired reduced pressure to which the tissue site 105 should be applied. The desired tissue site pressure will vary from tissue site to tissue site, but will generally be chosen based on the type of tissue making up the tissue site, the type of injury or wound (if any), the medical condition of the patient, and the preference of the attending physician. After selecting the desired target pressure (TP), the reduced pressure source 110 is controlled to achieve the target pressure (TP) desired for application to the tissue site 105.

Figure 3:
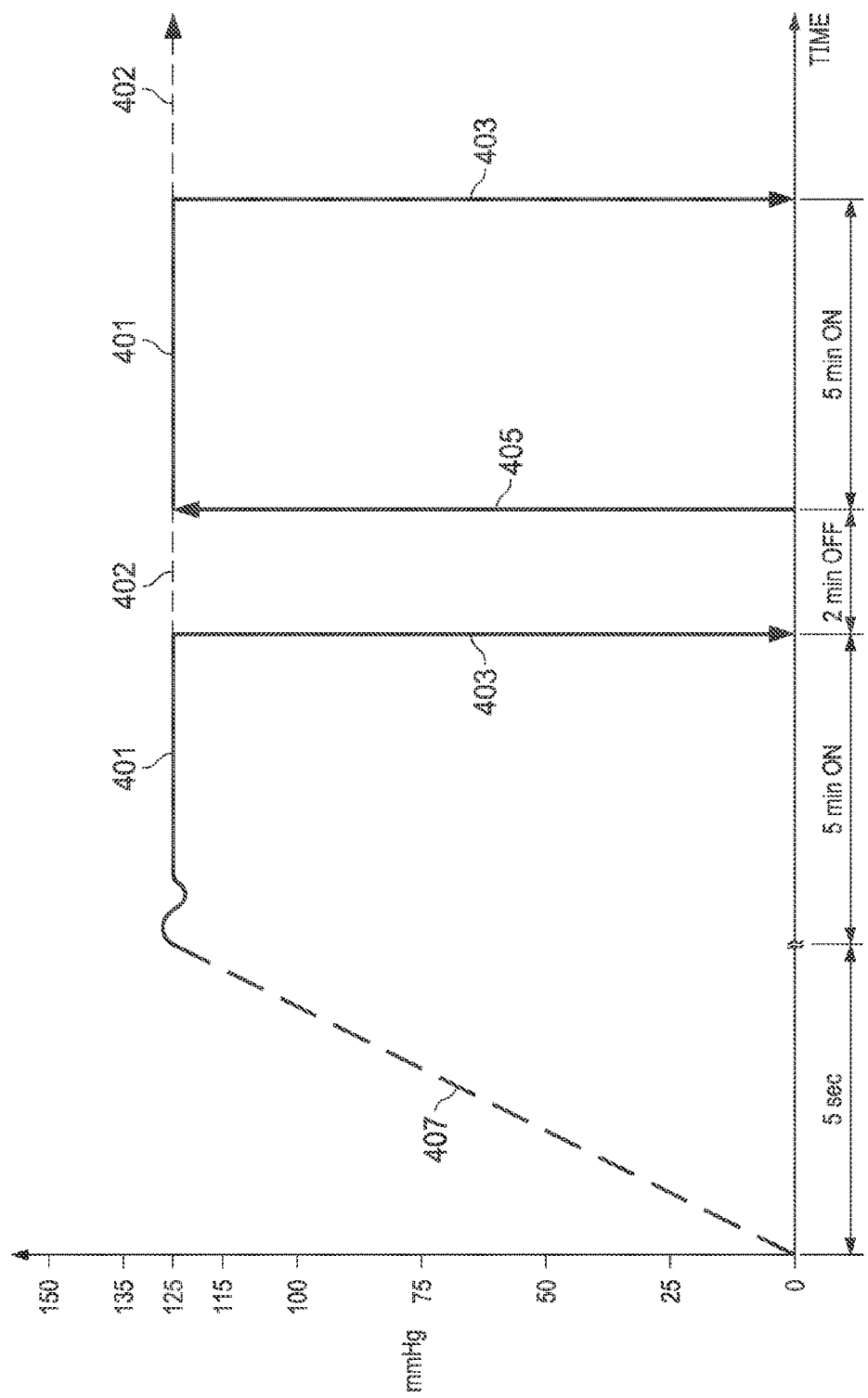
FIG. 3 is a graph illustrating pressure control of a motor-drive system in accordance with an illustrative embodiment of the example embodiment wherein the x-axis represents time in minutes (min) and/or seconds (sec) and the y-axis represents pressure generated by a pump in Torr (mmHg) that varies with time in a continuous control mode and an intermittent mode that may be used in the reduced pressure therapy system of FIG. 1.

Referring more specifically to FIG. 3, the target pressure (TP) may be set by the user in a continuous mode as indicated by solid line 401 and dotted line 402 wherein the wound site pressure (WP) is applied to the tissue site 105 until the user deactivates the reduced pressure source 110. The target pressure (TP) may also be set by the user in an intermittent mode as indicated by solid lines 401, 403 and 405 wherein the wound site pressure (WP) is cycled between the target pressure (TP) and atmospheric pressure. For example, the target pressure (TP) may be set by the user at 125 mmHg for a specified period of time (e.g., 5 min) followed by the therapy being turned off for a specified period of time (e.g., 2 min) as indicated by lines 403 by venting the tissue site 105 to the atmosphere, and then repeating the cycle by turning the therapy back on as indicated by line 405 which consequently forms a square wave pattern between the target pressure (TP) level and atmospheric pressure.

It should be understood that the increase of the wound site pressure (WP) at the tissue site 105 from the local ambient pressure to the target pressure (TP) is not instantaneous, but rather limited depending on the type of therapy equipment and the dressing. For example, the reduced pressure source 110 and the dressing 115 may have an initial rise time as indicated by the dashed line 407 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system is operating in the intermittent mode, the repeating rise time 405 may be a value substantially equal to the initial rise time 407.

In some embodiments, the target pressure (TP) may also be a variable target pressure (VTP) controlled or determined by controller 170 that varies in a dynamic pressure mode. For example, the variable target pressure (VTP) may vary between a maximum and minimum pressure value that may be set as an input by a user as the range of reduced pressures desired for therapy at the tissue site 105. The variable target pressure (VTP) may also be processed and controlled by controller 170 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 105. For example, the variable target pressure (VTP) may be a reduced pressure that provides an effective treatment by applying reduced pressure to tissue site 105 in the form of a triangular waveform varying between 50-125 mmHg with a rise time set at +25 mmHg/min and a descent time set at −25 mmHg/min In another embodiment of a reduced-pressure therapy system 100, the variable target pressure (VTP) may be a reduced pressure that applies reduced pressure to tissue site 105 in the form of a triangular waveform varying between 25-125 mmHg with a rise time set at a rate of +30 mmHg/min and a descent time set at −30 mmHg/min. Again, the type of system and tissue site determines the type of reduced pressure therapy to be used.

After selecting the target pressure (TP), the reduced pressure source 104 is operated to achieve the desired pressure at the tissue site 105 by controlling the pump pressure (PP). In many cases, the reduced pressure source 110 to be operated at a higher pump pressure (PP) than that of the target pressure (TP) due to pressure losses between the reduced pressure source 110 and the tissue site 105. Moreover, the head pressure of exudates and other fluids within the conduits may result in a reduction of vacuum pressure at the tissue site 105. The height of the canister 140 above the tissue site 105 may determine the amount of head pressure imposed on the tissue site 105 by fluid in the conduits. For exudates and fluids with a density similar to water, the head pressure imposed by one foot of fluid is almost 25 mmHg Some fluids withdrawn from the tissue site 105 may be even heavier or more viscous than water, and therefore have a more pronounced effect on pressure losses at the tissue site 105.

Figure 4:
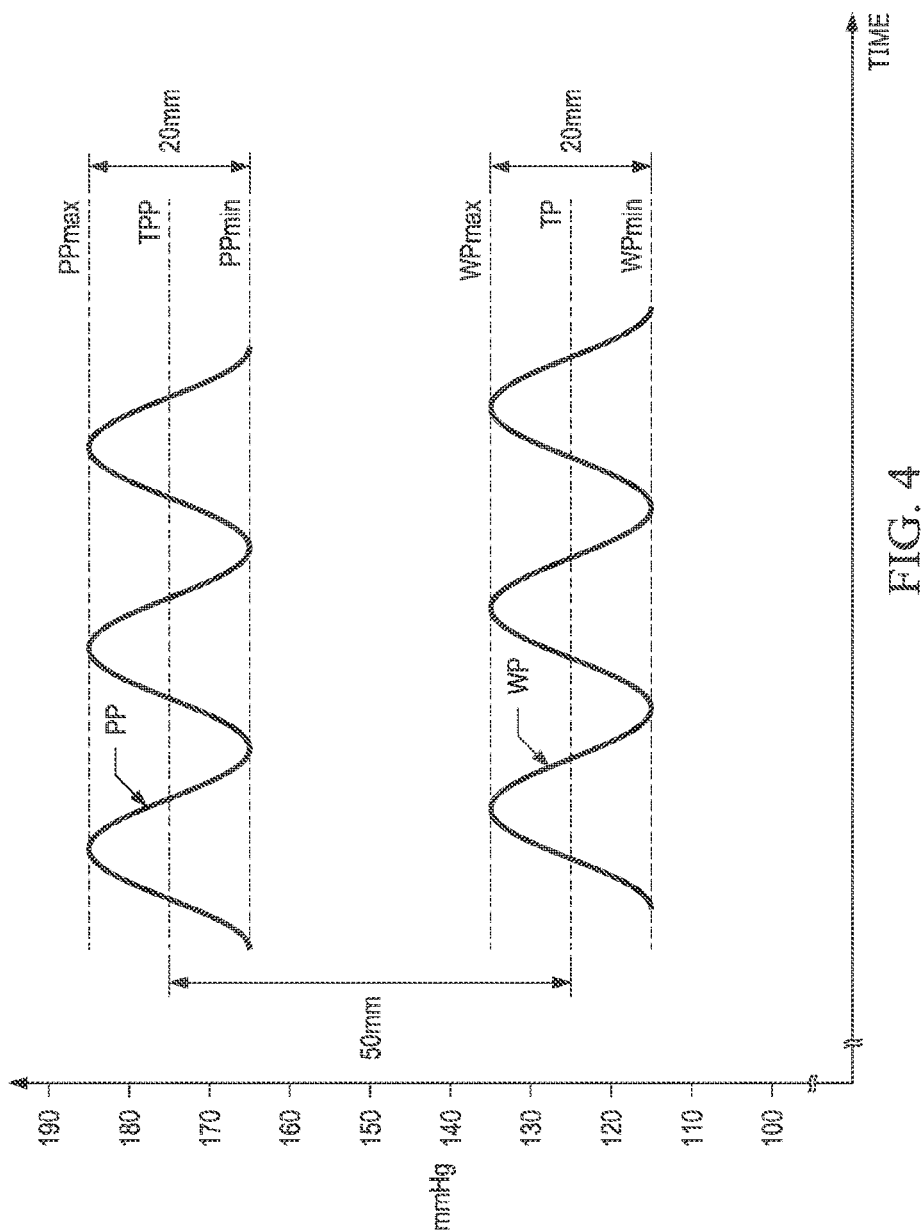
FIG. 4 is a graph illustrating pressure control of a motor-drive system in accordance with an illustrative embodiment of the example embodiment wherein the x-axis represents time in minutes (min) and/or seconds(sec) and the y-axis represents pressure generated by a pump in Torr (mmHg) that compares a manipulated variable, i.e., a tissue site or wound site pressure (WP) at a tissue site, and a control variable, i.e., a pump pressure (PP), for use with a PID controller and/or a bang-bang controller.
Figure 5:
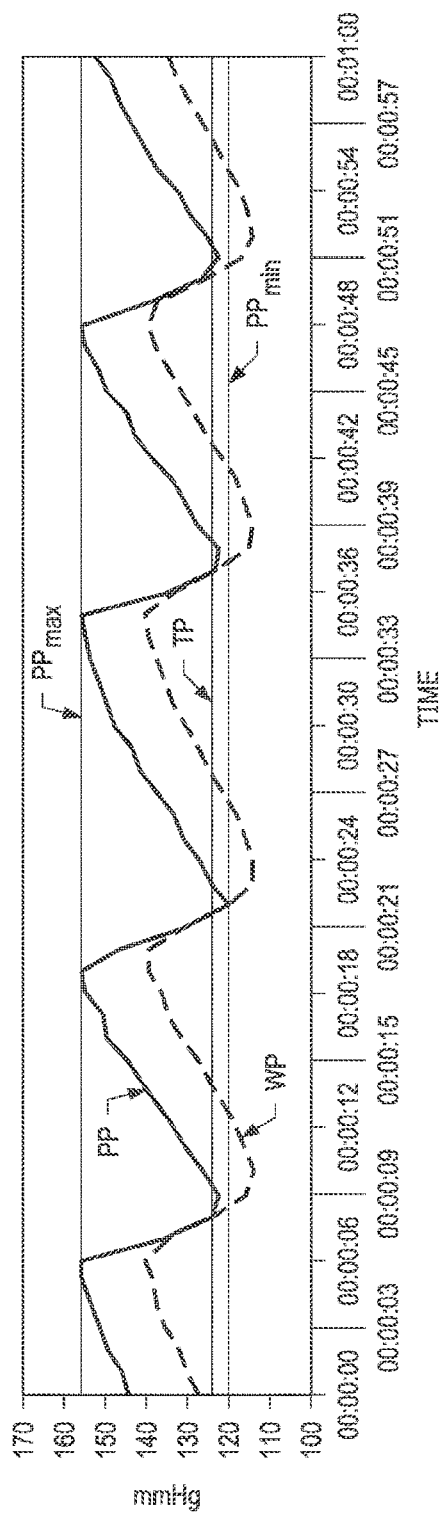
FIGS. 5 and 5A/B are graphs illustrating pressure control for a bang-bang controller in accordance with an illustrative embodiment of the example embodiment wherein the x-axis represents time in seconds(sec) and the y-axis represents pressure generated by a pump in Torr (mmHg) that varies with time in an continuous control mode and wherein the pressure control of the bang-bang controller is subjected to a larger head pressure created by the reduced-pressure's therapy system of FIG. 1 as shown in FIG. 5 compared to the smaller head pressure shown in FIGS. 5A/B, FIG. 5B having an expanded vertical pressure scale than that shown in FIG. 5A.
Figure 5A:
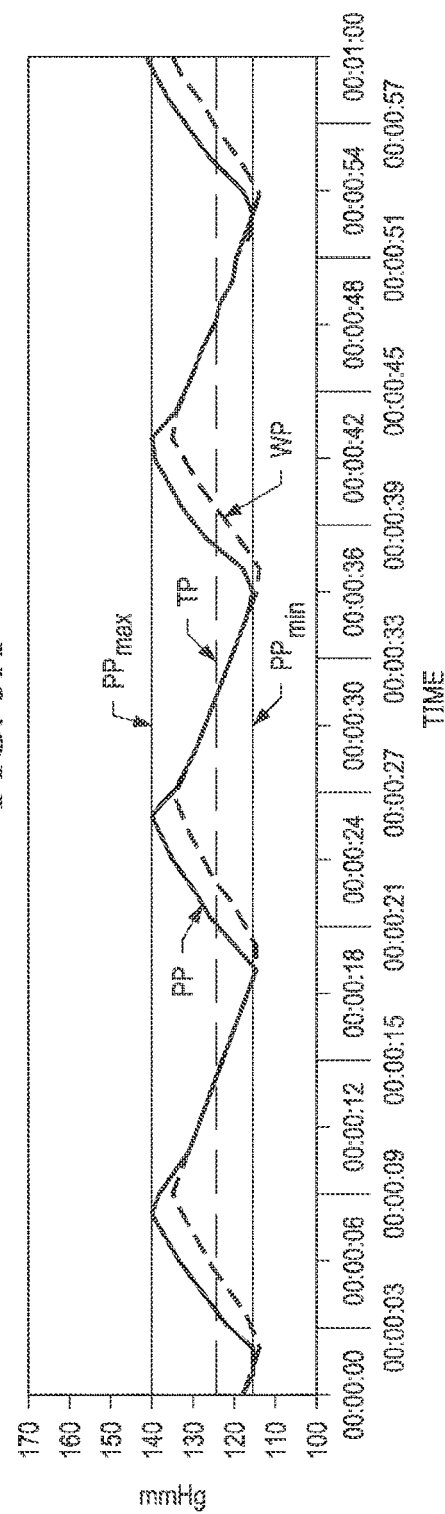
Figure 5B:
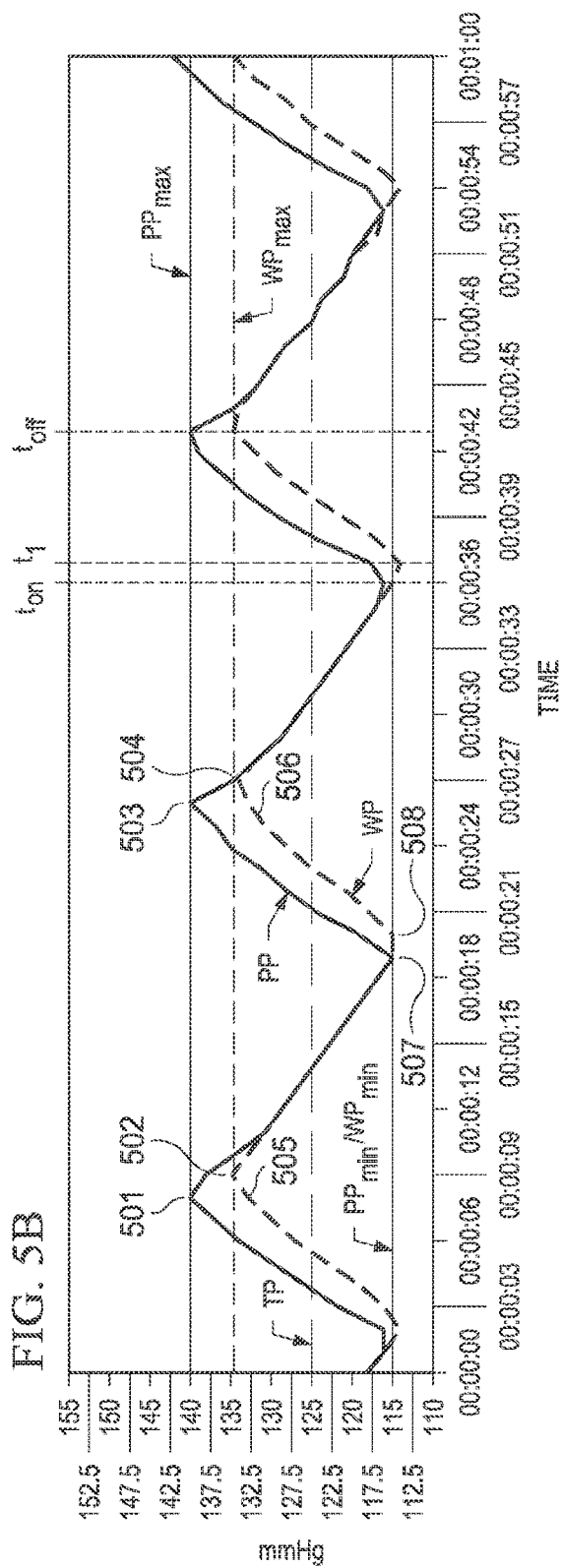

Referring to FIG. 4 as an example of the potential losses caused by the weight of fluid in the conduits, the target pressure (TP) prescribed for a particular tissue site may be −125 mm Hg wherein the wound site pressure (WP) varies as the reduced pressure is applied to the tissue site 105. (It should be understood that the steady sinusoidal variations of the wound site pressure (WP) shown in FIG. 4 are only explanatory and not representative of the actual variations of the wound site pressure (WP) under normal operational conditions such as, for example, the variations shown in FIGS. 5, 5A and 5B.) If the canister 140 is positioned two feet above the tissue site 105, and if the delivery tube 135 between the canister 140 and tissue site 105 is completely full of fluid, the head pressure imposed by that fluid could create a pressure differential (δP) of approximately 50 mmHg as shown in FIG. 4. This particular example occurs when a tissue site is located on a lower extremity of a patient such as a foot and the canister 140 is mounted near or above the patient's head (e.g., on an IV pole when the patient is in a wheelchair). Therefore, if the head pressure of fluid in the delivery tube 135 is approximately 50 mmHg, the pressure pump 112 needs to provide a pump pressure (PP) rising to a maximum pump pressure value (PPmax) of approximately 185 mmHg and dropping to a minimum pump pressure value (PPmin) of approximately 165 mmHg (a median target pump pressure (TPP) of approximately 175 mmHg) to yield a target pressure (TP) at the tissue site 105 of approximately 125 mmHg The controller 170 may also be programmed and controlled by a user to maintain the target pressure (TP) within an acceptable range of pressures. For example, if the target pressure (TP) is set at 125 mmHg as the desired therapeutic pressure for the tissue site 105, a user may desire that the wound site pressure (WP) varies by no more than ±10 mmHg from the desired target pressure (TP) so that the wound site pressure (WP) is controlled between a minimum wound site pressure value (WPmin) of 115 mmHg and a maximum wound site pressure value (WPmax) of 135 mmHg, i.e., a differential wound site pressure range (δWP) of about 20 mmHg Therefore, assuming for this example that there is a head pressure approximately 50 mmHg as described above, the pump pressure (PP) must also be variable by ±10 mmHg from the target pump pressure (TPP) so that the pump pressure (PP) may be varied in a range extending from the minimum pump pressure value (PPmin) of approximately 165 mmHg to the maximum pump pressure value (PPmax) of approximately 185 mmHg, i.e., a differential pump pressure (δTTP) of about 20 mmHg Controlling the pump pressure (PP) to stay within this range indirectly maintains the wound site pressure (WP) within a range extending from the minimum wound site pressure value (WPmin) of approximately 115 mmHg to the maximum wound site pressure value (WPmax) of approximately 135 mm Referring to FIG. 5 as an example of wound site pressure (WP) variations under normal operating conditions in contrast to the example illustrated in FIG. 4, the pressure differential (δP) between the pump pressure (PP) and the wound site pressure (WP) is the result of a fairly high leakage rate (LR) of approximately 300 cc/min in the dressing 115 and other components in the system. In this example, the wound site pressure (WP) is being controlled to cycle between approximately 135 mmHg and 115 mmHg as described above by providing a pump pressure (PP) that rises to a maximum pump pressure value (PPmax) of approximately 155 mmHg and drops to a minimum pump pressure value (PPmin) of approximately 120 mmHg to yield a target pressure (TP) at the tissue site 105 of approximately 125 mmHg Thus, the pressure differential (δP) is approximately 15 mmHg which is much less than the pressure differential of approximately 50 mmHg resulting from the head pressure in the example associated with FIG. 4 above. FIGS. 5A and 5B illustrate yet another example wherein the pressure differential (δP) between the pump pressure (PP) and the wound site pressure (WP) is the result of a lower leakage rate (LR) of approximately 50 cc/min in the dressing 115 and other components in the system. In this example, the wound site pressure (WP) is again being controlled to cycle between approximately 135 mmHg and 115 mmHg by providing a pump pressure (PP) that rises to a maximum pump pressure value (PPmax) of 140 mmHg and drops to a minimum pump pressure value (PPmin) of 115 mmHg to yield a target pressure (TP) at the tissue site 105 of approximately 125 mmHg Thus, the pressure differential (δP) is approximately 5 mmHg which is even less than the pressure differential in the previous example The pressure variations shown in FIG. 5B are the same as those shown in FIG. 5A except only that the pressure variations in FIG. 5B are shown with an expanded pressure scale.

The controller 170 may also comprise a bang-bang controller (not shown) which is also referred to as an on-off controller, or a hysteresis controller. The bang-bang controller is a feedback controller that switches abruptly between two states, e.g., between on and off. Essentially, the bang-bang controller may apply an all-or-nothing form of control. A bang-bang controller may be used to generate the pressure variations described generally above in conjunction with FIGS. 5, 5A and 5B. Referring more specifically to FIG. 5B, and continuing with that general description, the bang-bang controller may operate in one mode as follows. For example, when the wound site pressure (WP) drops too low to the minimum wound site pressure value (WPmin), the pressure pump 112 is turned on with an applied voltage (VA) greater than the stall voltage, i.e., the bang-bang on voltage (VON) at a start time (ton), to increase the pump pressure (PP) to the maximum pump pressure (PPmax). Although an increase in the pump pressure (PP) may slightly lag the application of the applied voltage (VA), the increasing pump pressure (PP) eventually causes the wound site pressure (WP) to increase as well as shown at time t1.

In some embodiments, the bang-bang voltage (VON) continues to be applied until the wound site pressure (WP) reaches the maximum wound site pressure (WPmax). When the maximum wound site pressure (WPmax) is reached or exceeded, the pressure pump 112 is turned off at an off time (toff) so that no pump pressure (PP) is applied allowing the residual pressure in the reduced pressure therapy system 100 to decrease as a result of the leakage in the system. The pressure pump 112 remains off until the wound site pressure (WP) is again less than or equal to the minimum wound site pressure value (WPmin). In some embodiments, the residual pressure may also be reduced more quickly by opening a relief valve (not shown) that vents air pressure from the system.

In some embodiments, the bang-bang voltage (VON) to be applied until the pump pressure (PP) reaches the maximum pump pressure value (PPmax) or the wound site pressure (WP) reaches the maximum wound site pressure value (WPmax), whichever occurs first. When either one of these maximum values is reached or exceeded, the pressure pump 112 is turned off at an off time (toff) so that no pump pressure (PP) is applied allowing the residual pressure in the reduced pressure therapy system 100 to decrease as a result of the leakage in the system. The pressure pump 112 remains off until the wound site pressure (WP) is again less than or equal to the minimum wound site pressure value (WPmin) or the pump pressure (PP) is less than or equal to the minimum pump pressure value (PPmin), whichever occurs first. In some embodiments, the residual pressure may also be reduced more quickly by opening the relief valve.

The bang-bang controller switches between these two states wherein the pressure pump 112 is turned on when the wound site pressure or the pump pressure drops too low in a descending mode and turns the pressure pump 112 off when the wound site pressure or pump pressure rises too high in an ascending mode. The bang-bang controller allows the wound site pressure (WP) to oscillate proximate the target pressure (TP) of 125 mmHg as contained between the two limits of a hysteresis control band that a user programs into the system controller 170, e.g., the minimum wound site pressure value (WPmin) of 115 mmHg and the maximum wound site pressure value (WPmax) of 135 mmHg The wound site pressure (WP) is not pulled back within the hysteresis control band or wound site pressure range (δWP) of 20 mmHg unless the wound site pressure (WP) exceeds either one of these limits. The bang-bang controller maintains the wound site pressure (WP) substantially within this range because the bang-bang controller does not need to overcompensate for leakage in a low-leakage environment. The controller 170 may further include an input for a user/caregiver to set one or more limits of the hysteresis control band and there may be a plurality of hysteresis control bands. The system may further include an output for the user/caregiver and the output may be a hysteresis control band status indicator, for instance the hysteresis control band status indicator may indicate whether the hysteresis control band is currently set to narrow or wide as discussed herein.

In some embodiments, the system controller 170 may also include a Proportional Integral Derivative (PID) controller (not shown) that provides a control loop feedback mechanism that calculates an error value as the difference between a measured process variable and a desired set point or target, in this case the wound site pressure (WP) and the corresponding target pressure (TP) at the tissue site 105, respectively. PID controllers are well-known by those skilled in the art as providing proportionality information, historical information, and time rate of change information to maintain the wound site pressure (WP) close to the target pressure (TP). The PID summation is used to adjust the process, in this case the reduced pressure therapy process, by a control element such as the power or voltage supplied to a DC motor 114, i.e. the applied voltage (VA), which is directly related to the pump pressure (PP) as described above. The applied voltage (VA) may be varied as described above by adjusting the Pulse-Width Modulation (PWM) to achieve the desired pump pressure (PP) necessary to compensate for the leakage of the dressing 115 and/or the pressure head referred to above. The response of the PID controller is dependent on the responsiveness of the PID controller to an error, the degree to which the PID controller overshoots the set-point, e.g., the target pressure (TP), and the degree of system oscillation, e.g., the degree of oscillation of the wound site pressure (WP) within the acceptable range described above. Although a preferred embodiment of the PID controller is a digital controller, the PID controller may also be an analog controller or a simple RC circuit. The analog or digital PID controller may be implemented in hardware components or software as part of a program logic controller well-known in the art.

After the first pressure sensor 155 measures the wound site pressure (WP), the PID controller adjusts the pump pressure (PP) by supplying the applied voltage (VA) necessary for adjusting the wound site pressure (WP) back to the target pressure (TP), i.e., the pump pressure correction (δPP). The pump pressure correction (δPP) is the additional pressure needed to maintain the wound site pressure (WP) at the desired target pressure (TP), e.g., 125 mmHg, and may be calculated every few seconds. Consequently, the PID control varies the applied voltage (VA) to the DC motor 114 to achieve a pump pressure (PP) between a minimum pump pressure value (PPmin) and a maximum pump pressure value (PPmax) which maintains the wound site pressure (WP) proximate the target wound site pressure (TP).

Figure 6:
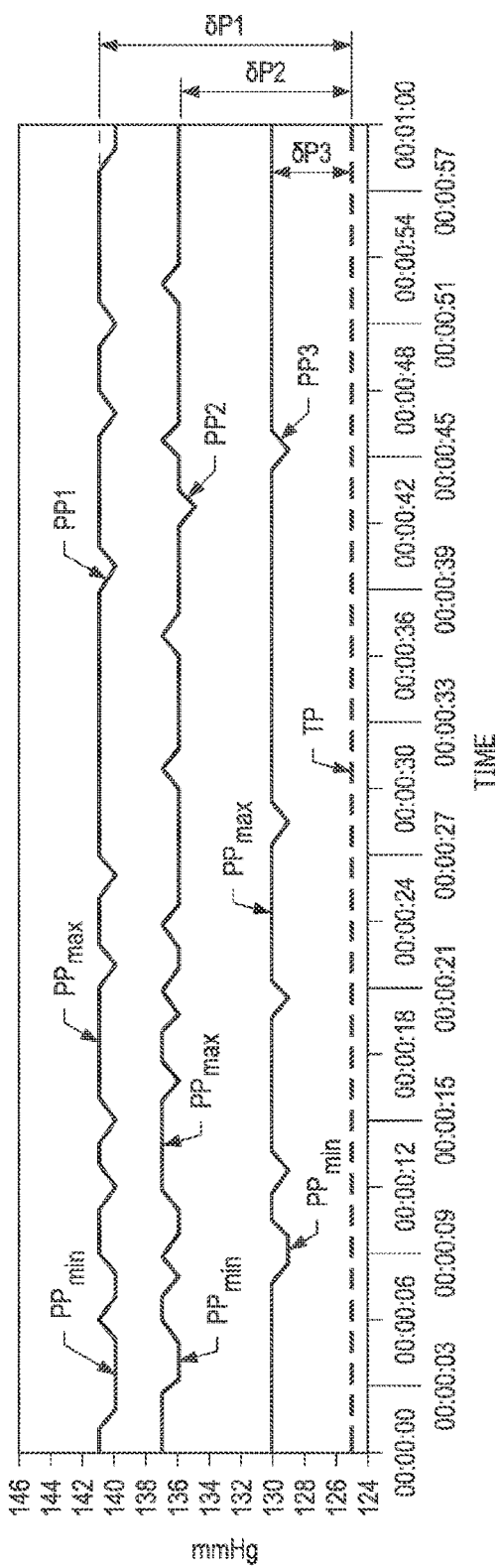
FIG. 6 is a graph illustrating pressure control for a PID controller in accordance with an illustrative embodiment of the example embodiment wherein the x-axis represents time in seconds(sec) and the y-axis represents pressure generated by a pump in Torr (mmHg) that varies with time in an continuous control mode and wherein the horizontal time scale is substantially the same as the horizontal timescale shown in FIG. 5B for comparing pressure control with that of the bang-bang controller.

Referring more specifically to FIG. 6 as an example of maintaining the wound site pressure (WP) under normal operating conditions of a PID controller in contrast to the example illustrated in FIG. 4, the pressure differential (δP) between the pump pressure (PP) and the wound site pressure (WP) is the result of different leakage rates (LR) as illustrated by the three examples including the first pump pressure (PP1), the second pump pressure (PP2), and the third pump pressure (PP3). In the first example, the first pump pressure (PP1) has a relatively large pressure differential (δP1) of approximately 15-16 mmHg resulting from a fairly high leakage rate (LR) of approximately 350 cc/min. The first pressure (PP1) is varied by the PID controller between a maximum pump pressure value (PPmax) and a minimum pump pressure value (PPmin) to maintain the wound site pressure (WP) at the target pressure (TP) of 125 mmHg In other words, the PID controller varies the first pump pressure (PP1) between 140 mmHg and 141 mmHg to maintain the wound site pressure (WP) at the target pressure (TP) of 125 mmHg In the second example, the second pump pressure (PP2) also has a relatively large pressure differential (δP2) of approximately 11-12 mmHg resulting from a fairly high leakage rate (LR) of approximately 250 cc/min and is varied by the PID controller between a maximum pump pressure value (PPmax) and a minimum pump pressure value (PPmin) to maintain the wound site pressure (WP) at the target pressure (TP) of 125 mmHg In other words, the PID controller varies the second pump pressure (PP2) between 136 mmHg and 137 mmHg to maintain the wound site pressure (WP) at the target pressure (TP) of 125 mmHg Fundamentally, the difference between these two examples is that the higher leakage rate (LR) requires a larger pressure differential (δP) to maintain the wound site pressure (WP) at the same target pressure (TP). The third example illustrates the same difference wherein the third pump pressure (PP3) also has a much smaller pressure differential (δP3) of approximately 4-5 mmHg resulting from a lower leakage rate (LR) of approximately 100 cc/min and is varied by the PID controller between 129 mmHg and 130 mmHg to maintain the wound site pressure (WP) at the target pressure (TP) of 125 mmHg.

Unlike the bang-bang controller, the PID controller does not switch the pressure pump 112 on and off, but rather continuously controls the application of the pump pressure (PP) between the maximum and minimum pressure values, (PPmax) and (PPmin), to maintain the wound site pressure (WP) at a relatively constant level, e.g., at a target pressure (TP) all of 125 mmHg as shown by the dashed line, rather than allowing it to vary between a maximum and minimum pressure value, (WPmax) and (WPmin) as shown with the bang-bang controller. Therefore, the extent to which the pump pressure (PP) drops towards the minimum pump pressure value (PPmin), the more that the PID controller increases the applied voltage (VA) being provided to the DC motor 114. Correspondingly, the further the wound site pressure (WP) varies from the target pressure (TP), the more the PID controller responds by adjusting the applied voltage (VA) being provided to the DC motor 114. The action taken to increase or decrease the applied voltage (VA) is proportional to the degree that the wound site pressure (WP) provided by the reduced pressure system diverges from the target wound site pressure (TP). The PID controller continuously operates in order to keep the wound site pressure (WP) as close to the target wound site pressure (TP) as possible, especially for high leakage rates (LR). Consequently, the PID controller causes the reduced pressure therapy system 100 to run smoother than the bang-bang controller as shown when comparing the wound site pressure (WP) variations of FIGS. 6 and 5, respectively, because the PID controller maintains the wound site pressure (WP) closer to the target wound site pressure (TP) on average, while the bang-bang controller allows the wound site pressure (WP) to oscillate between the two limits as described above.

When the flow rate (FR) is small enough to indicate a low leakage condition, e.g., when the pump pressure (PP) or the wound site pressure (WP) is decreasing at a very slow rate toward their respective minimum pressure values, i.e., (PPmin) or (WPmin), the bang-bang controller may provide a sufficiently smooth wound site pressure (WP) during treatment while conserving battery power and reducing noise by virtue of the pressure pump 112 being intermittently turned off during the same treatment period. For example, the DC motor 114 and pressure pump 112 are turned off for a significant percentage of time during the one minute period shown in FIG. 5B, but run continuously when the PID controller is operative as shown in FIG. 6. Hence, it is desirable to keep the bang-bang controller running during treatment sessions as much as possible for low leakage conditions such as, for example, when the flow rate (FR) is less than or equal to a fixed target flow rate (TFR) which represents a low leak condition, but switch to the PID controller when the flow rate (FR) is greater than the fixed target flow rate (TFR) which represents a high leak condition. Consequently, another example embodiment of the system controller 170 includes both the PID controller and the bang-bang controller, i.e., a hybrid controller, and additional processing that switches between them depending on the degree of leakage of the reduced pressure therapy system 100 regardless of the location of the leaks or leakage.

Thus, the system controller 170 may be programmed to use the bang-bang controller in conjunction with the PID controller operating as described above to enable or disable the PID controller depending on a specific switching condition relating to the amount of air leakage created by the dressing 115 or other components of the reduced pressure therapy system 100 that affect the flow rate (FR). Using such a hybrid controller would be preferable to utilizing only a PID controller which runs continuously during the continuous control mode as described above (or the enabled portions of an intermittent control mode as described above) to more tightly maintain the wound site pressure (WP) at the target wound site pressure (TP), but may continually generate noise and more rapidly drain the battery driving the DC motor 114. The hybrid controller may engage the bang-bang controller so that the DC motor 114 is turned on and off to conserve battery power and reduce noise generated by the pressure pump 112 during therapy treatments. The controller 170 may further include an input for a user/caregiver to set one or more target flow rates (TFR).

In some embodiments, the user/caregiver may set the target flow rates (TFR) as the switching condition for determining whether the dressing 115 or other components are in a high leakage state or a low leakage state. For example, if the flow rate (FR) is greater than the fixed target flow rate (TFR), i.e., a high leak condition, the bang-bang controller is disabled so that the PID controller takes over in order to keep the wound site pressure (WP) as close to the target wound site pressure (TP) as possible. However, if the flow rate (FR) is less than or equal to the fixed target flow rate (TFR), i.e., a low leak condition, the bang-bang controller is enabled to contain the wound site pressure (WP) within the differential wound site pressure ($\delta$WP) range while conserving battery power and reducing noise from the pressure pump 112. For example, the fixed target flow rate (TFR) may be 65 cc/min. As indicated above, it is desirable to keep the bang-bang controller running as much as possible during treatments when the dressing 115 is in a low leakage condition. For example, the system controller 170 may engage the bang-bang controller when the flow rate (FR) is less than or equal to the fixed target flow rate (TFR), but switch back to the PID controller when the flow rate (FR) is greater than the fixed target flow rate (TFR) as a result of additional leakage that develops in the dressing 115 because the patient moving around which ultimately creates a high leak condition.

In another embodiment, the bang-bang controller may have a dual target flow rate (TFR) capability wherein the system controller 170 further includes an input for a user to set two target flow rates (TFR) as switching conditions for determining whether the dressing 115 or other components are in a high leakage state or a low leakage state: an ascending target flow rate (TFRA) when the bang-bang controller is enabled with an increasing flow rate (FR) and a descending target flow rate (TFRD) when the PID controller is enabled with a decreasing flow rate (FR). In one embodiment, both the ascending target flow rate (TFRA) and the descending target flow rate (TFRD) are greater than the fixed target flow rate (TFR) so that the system controller 170 switches more quickly from the PID controller to the bang-bang controller and more slowly from the bang-bang controller to the PID controller. For example, the ascending target flow rate (TFRA) and the descending target flow rate (TFRD) may both be set to about 80 cc/min which is higher than the fixed target flow rate (TFR) of 65 cc/min in the previous example. In yet another embodiment, the ascending target flow rate (TFRA) may also be greater than the descending target flow rate (TFRD) so that the system controller 170 switches even more quickly from the PID controller to the bang-bang controller and even more slowly from the bang-bang controller to the PID controller. In this case, the system controller 170 favors the benefits derived from using the bang-bang controller as opposed to the deficiencies associated with the continuous operation of the PID controller. For example, the ascending target flow rate (TFRA) may be 75 cc/min and the descending target flow rate (TFRD) may be about 85 cc/min. If the PID controller is currently enabled in a high leak condition wherein the flow rate (FR) is decreasing, the descending target flow rate (TFRD) would be set at 85 cc/min rather than 65 cc/min so that the system controller 170 switches more quickly from the PID controller to enable the bang-bang controller. Alternatively, if the bang-bang controller is enabled in a low leak condition wherein the flow rate (FR) is increasing, the first ascending target flow rate (TFRA) would be set at 75 cc/min rather than 65 cc/min so that the system controller 170 switches more slowly to disable the bang-bang controller.

In one embodiment, controller 170 may provide an output signal to the indicator 172 to emit a visual and/or audible signal in response to the wound site pressure (WP) at tissue site 105, as measured by first pressure sensor 155, being nonresponsive to increasing the pump pressure (PP). For example, the indicator 172 may be a light emitting diode (LED) that provides a visual signal. In this embodiment, indicator 172 illuminates in response to the wound site pressure (WP) at tissue site 105 being nonresponsive to an increasing pump pressure. In another embodiment, indicator 172 is a sound emitting device, such as a speaker. In this embodiment, indicator 172 emits a sound in response to the wound site pressure (WP) at tissue site 105 being nonresponsive to an increasing pump pressure. The controller 170 may provide other output signals indicating whether the negative-pressure therapy system is in a low or high leak condition.

Figure 7:
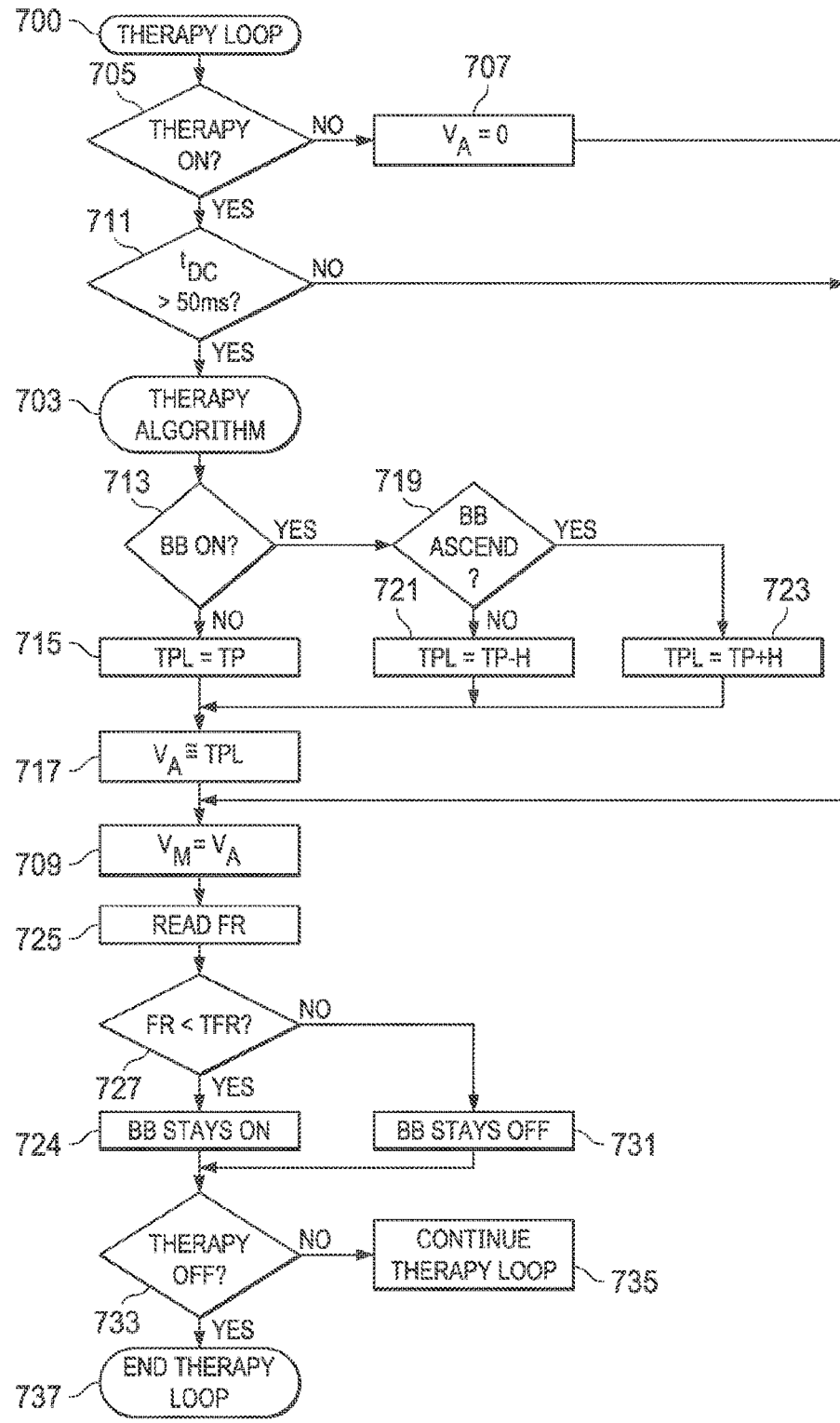
FIG. 7 is a flowchart illustrating a process or therapy loop for controlling reduced pressure at a tissue site that may be stored on the system controller of FIG. 1 including a therapy algorithm for selecting the appropriate control band for controlling reduced pressure at a tissue site in accordance with an illustrative embodiment of the example embodiment.

Referring now to FIG. 7, an example embodiment of a method or process for controlling the wound site pressure (WP) as implemented on the system controller 170 as described above or, alternatively, on another example embodiment of the system controller 170 is shown. The controller 170 and other components may implement this process as described above according to a therapy loop 700 illustrated as the flowchart in FIG. 7. The therapy loop 700 includes a therapy algorithm 703 for selecting the appropriate controller, i.e., the PID controller or the bang-bang controller, for controlling the delivery of reduced pressure to the tissue site while conserving power and reducing noise from the pressure pump 112 and the DC motor 114 at the same time. The controller 170 first checks to see if the negative-pressure therapy system 100 has been turned on at 705 so that if the reduced-pressure therapy system 100 is not on, the applied voltage (VA) is set to 0 V at 707 and applied to the DC motor 114 as a new motor voltage (VM) at 709 so that the DC motor 114 is not running. If the reduced-pressure therapy system 100 is turned on, the system controller 170 checks to determine whether enough time has elapsed at 711 to engage the therapy algorithm 703, i.e., the duty cycle therapy time (tDC). The duty cycle of the therapy algorithm 703 may be, for example, about 50 ms. Thus, if less than 50 ms transpires since the therapy algorithm 703 was last calculated, the DC motor voltage (VM) remains set at the previously applied voltage (VA) at 709. The duty cycle of the therapy loop 700 itself may be, for example, 10 ms without engaging the therapy algorithm 703. However, if more than 50 ms have transpired, the system controller 170 recalculates the therapy algorithm 703 and proceeds to check the current wound site pressure (WP) and/or the pump pressure (PP) at 713 with respect to their corresponding maximum and minimum wound site pressure and pump pressure values as described above, i.e., (WPmax) and (WPmin), and (PPmax) and (PPmin), respectively.

The therapy algorithm 703 begins by determining whether the bang-bang controller is active or not at 713. If the PID controller is engaged and the bang-bang controller is not, a local pump pressure (PPL) is set at a current pump pressure (PPC) at 715. As described above, the PID control adjusts the applied voltage (VA) to the DC motor 114 to achieve a pump pressure (PP) between the minimum pump pressure value (PPmin) and the maximum pump pressure value (PPmax) to maintain the wound site pressure (WP) proximate the target wound site pressure (TP). Referring back to FIG. 6 as an example, the PID controller varies the first pump pressure (PP1) between 140 mmHg and 141 mmHg to maintain the wound site pressure (WP) at the target pressure (TP) of 125 mmHg and continues to control the pump pressure (PP) during a high leakage condition. The controller 170 determines the value of applied voltage (VA) corresponding to the current pump pressure (PPC) at 717 and applies that voltage as the DC motor voltage (VM) at 709. However, if the bang-bang controller is engaged or active as shown in FIG. 5B, the therapy algorithm 703 determines whether the bang-bang controller is ascending or descending at 719.

When the wound site pressure (WP) drops too low in the descending mode, e.g., below the minimum wound site pressure value (WPmin) as described above, the pressure pump 112 is turned on with an applied voltage (VA) greater than the stall voltage, i.e., the bang-bang on voltage (VON), to increase the pump pressure (PP) to the maximum pump pressure (PPmax) in the ascending mode. The bang-bang on voltage (VON) continues to be applied until the pump pressure (PP) reaches the maximum pump pressure value (PPmax) as shown, for example, at 501 and 503, or the wound site pressure (WP) reaches the maximum wound site pressure value (WPmax) as shown, for example, at 502 and 504, whichever occurs first. When the wound site pressure (WP) is in the ascending mode, the therapy algorithm 703 sets the local target wound site pressure (TPL) at the target wound site pressure (TP) plus a hysteresis value (H) at 723. The hysteresis value (H) is the maximum amount of pressure that the wound site pressure (WP) should increase above the target wound site pressure (TP) when in the ascending mode before the bang-bang controller turns off the pressure pump 112 to protect the tissue site 105 from an excessive amount of reduced pressure that could be damaging. The hysteresis value (H) sets the upper limit above the target wound site pressure (TP) which is the maximum pressure value (WPmax). For example, if the hysteresis value (H) is 10 mmHg, the maximum wound site pressure value (WPmax) is set at 135 mmHg as shown in FIG. 5B. Because the wound site pressure (WP) normally trails the ascending pump pressure (PP) as shown by the wound site pressure peaks at 502 and 504, and the pump pressure peaks at 501 and 503, the wound site pressure (WP) is normally less than the maximum wound site pressure value (WPmax), e.g., about 132 mmHg at 505 and 506, when the pump pressure (PP) hits the maximum pump pressure value (PPmax), e.g., about 140 mmHg at 501 in 503. Consequently, the system controller 170 allows the bang-bang controller to continue regulating the application of reduced pressure, but does turn off the pressure pump 112 in the descending mode of the reduced pressure cycle.

Correspondingly, when the wound site pressure (WP) rises too high in the ascending mode, e.g., above the maximum wound site pressure value (WPmax) or the maximum pump pressure value (PPmax) as described above, the pressure pump 112 is turned off so that no pump pressure (PP) is applied allowing the residual pressure in the reduced pressure therapy system 100 to decrease in the descending mode as a result of the leakage in the system. The pressure pump 112 remains off until the wound site pressure (WP) is again less than or equal to the minimum wound site pressure value (WPmin) is shown, for example, at 508, or the pump pressure (PP) is less than or equal to the minimum pump pressure value (PPmin) as shown, for example, at 507, whichever occurs first. When the wound site pressure (WP) is in the descending mode as described above, the therapy algorithm 703 sets the local target wound site pressure (TPL) at the target wound site pressure (TP) minus the hysteresis value (H) at 721. The hysteresis value (H) is the minimum amount of pressure that the wound site pressure (WP) should decrease below the target wound site pressure (TP) when in the descending mode before the system controller 170 determines that the leakage rate (LR) has increased to a flow rate that is large enough to require the PID controller to maintain the wound site pressure (WP) closer to the target wound site pressure (TP) as described above. Thus, the hysteresis value (H) also sets the lower limit below the target wound site pressure (TP) which is the minimum pressure value (WPmin). For example, if the hysteresis value (H) is 10 mmHg, the minimum wound site pressure value (WPmin) is set at 115 mmHg as shown in FIG. 5B. Because the pump pressure (PP) normally follows the descending wound site pressure (WP) as shown between the pump and wound site pressure peaks at 501 and 502, respectively, and the pressure pump 112 and wound site pressure minimums that 507 and 508, respectively, the bang-bang controller turns the pressure pump 112 back on at 507 after which the wound site pressure (WP) begins to increase again in the ascending mode. Consequently, the system controller 170 allows the bang-bang controller to continue regulating the application of reduced pressure, and does so by turning on the pressure pump 112 in the ascending mode of the reduced pressure cycle. The bang-bang controller allows the wound site pressure (WP) to effectively oscillate around the target pressure (TP) of 125 mmHg as contained between the two limits that may be programmed into the system controller 170 separately using the minimum wound site pressure value (WPmin) of 115 mmHg and the maximum wound site pressure value (WPmax) of 135 mmHg, or using the hysteresis value (H) and the target pressure (TP). In either case, the bang-bang controller maintains the wound site pressure (WP) within a wound site pressure range (δWP), e.g., a hysteresis control band or wound site pressure range (δWP) of 20 mmHg.

After the therapy algorithm 703 sets the DC motor voltage (VM) to equal the applied voltage (VA) at 709 to reenter the therapy loop 700, the therapy loop 700 then reads the current flow rate (FR) measured by the system controller 170 at 725 and determines whether or not the current flow rate (FR) is less than the target flow rate (TFR) at 727. If the flow rate (FR) is less than the target flow rate (TFR) indicating a low leakage condition as described above, then the bang-bang controller stays on or is enabled as indicated at 729. However, if the flow rate (FR) is greater than or equal to the target flow rate (TFR) indicating a high leakage condition as described above, then the bang-bang controller stays off or is disabled as indicated at 731. Finally, the therapy loop 700 checks to see if the negative-pressure wound therapy system 100 has been turned off at 733 and, if not, continues the therapy loop as indicated at 735. If the negative-pressure therapy system 100 has been turned off, the therapy loop ends at 737.

The systems, apparatuses, and methods described herein may provide significant advantages. For example, PID control algorithms constantly adjust a negative-pressure source to maintain pressure within a specified tolerance, which can be inefficient in low-leak applications, drawing more power than a simple hysteresis control algorithm. Conversely, a hysteresis algorithm can work well in low-leak applications and uses relatively little power, but can cause a negative-pressure source to turn off and on frequently in high-leak applications, which can be noisy and increase power consumption. Hybrid control, as described herein, can combine the benefits of PID and hysteresis control algorithms to minimize power consumption and noise. If a negative-pressure therapy application has a low-leak, for example, a hybrid control algorithm can select a hysteresis control algorithm to minimize power consumption. If the application changes or develops a higher leak, a hybrid control algorithm can switch to a PID control algorithm to minimize noise.

Figure 8:
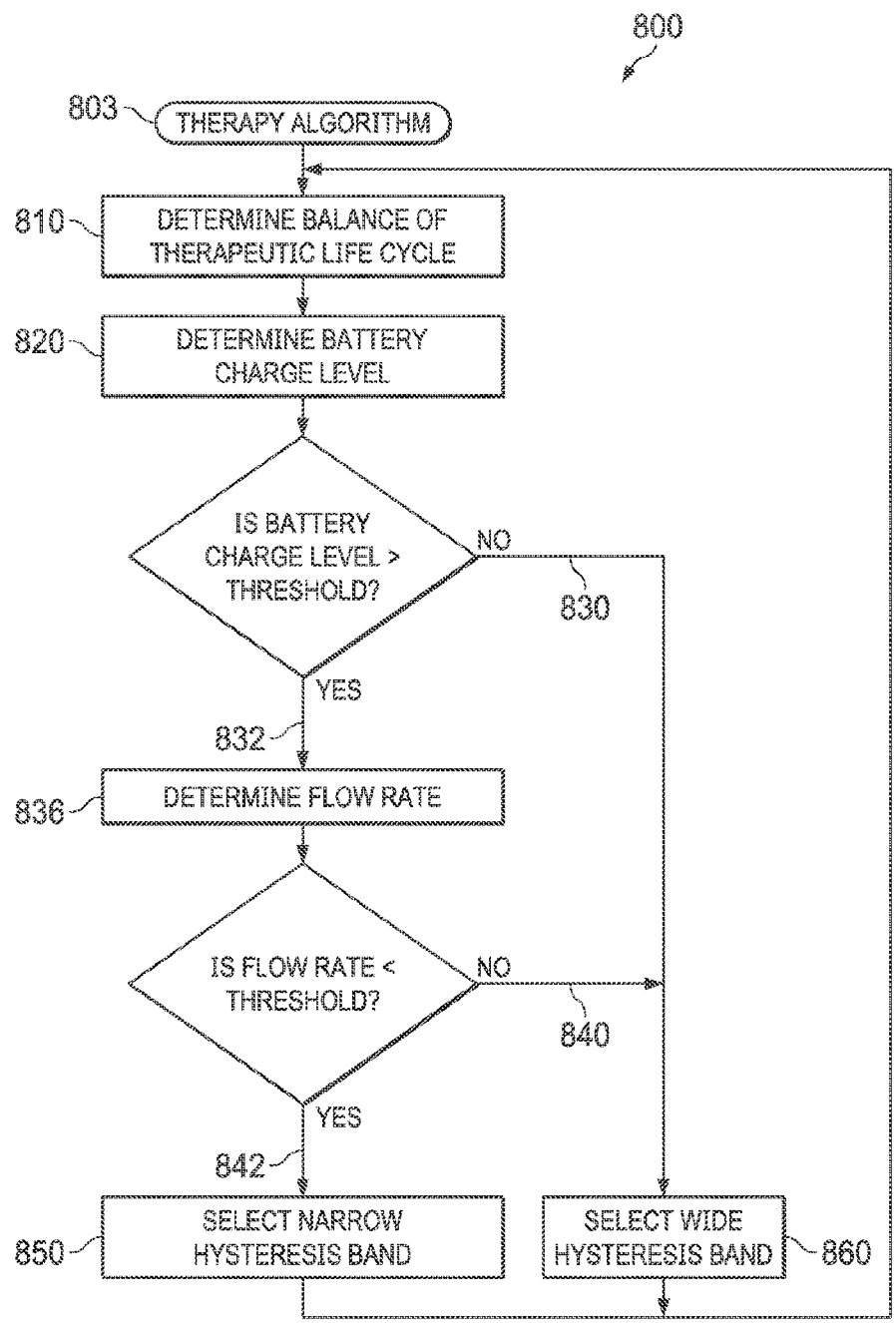
FIG. 8 is a flowchart illustrating a process or therapy loop for controlling reduced pressure at a tissue site that may be stored on the system controller of FIG. 1 including a therapy algorithm for selecting the appropriate control band for controlling reduced pressure at a tissue site in accordance with an illustrative embodiment of the example embodiment.

Referring now to FIG. 8, an example embodiment of a method or process for controlling the wound site pressure (WP) as implemented on the system controller 170 as described above or, alternatively, on another example embodiment of the system controller 170 is shown. The controller 170 and other components may implement this process as described above according to a therapy loop 800 illustrated as the flowchart in FIG. 8. The therapy loop 800 includes a therapy algorithm 803 for selecting 850, 860 the appropriate hysteresis control band for the bang-bang controller, i.e., the narrow hysteresis controller band 850 or alternatively the wide hysteresis control band 860, for controlling the delivery of reduced pressure to the tissue site while conserving power. In some embodiments, the therapy algorithm 803 may be used combination with other therapy algorithms, for example the therapy algorithm 703 described herein for selecting the appropriate controller or alternatively may be used as a standalone therapy algorithm 803.

The provision of negative-pressure therapy with negative-pressure therapy systems is increasingly being performed with smaller therapy device 100 that use batteries to provide power to a pump 112 rather than a connection to an electrical outlet. Use of batteries decreases the total power supply available to the therapy device 100. As a result, power drains that would be considered negligible in a therapy device 100 powered through an electrical outlet connection may significantly reduce the ability of the therapy device 100 to provide therapy for the duration of the therapeutic life cycle. A power drain refers to operation of the therapy device that requires use of electrical power, for example, operation of a pump 112 to generate reduced pressure. Power drains may be caused by low-level dressing leaks, for example, a low-level dressing leak can drain power from a battery of a therapy device 100 by repeatedly triggering operation of the therapy device 100 to maintain the necessary reduced pressure at the tissue site. These power drains shorten the useful life of the therapy device 100 before disposal of the therapy device 100, recharge of the battery, or battery replacement is required. Leak detection techniques may help to identify some leaks that may be then sealed by the user; however, low level leaks will challenge the most sensitive leak detection systems and may often go undetected.

In an example embodiment, the therapy device 100 may be a small portable disposable therapy device 100 powered by batteries and either a user/clinician may configure the system controller 170 for a 7-day (168-hour) therapeutic life cycle or the therapy device 100 may be preconfigured during manufacture for a 7-day therapeutic life cycle. The system controller 170 may further be configured to determine via a clock, counter, timer or the like how much of the therapeutic life cycle has been completed to date and thereby determine the balance of the therapeutic life cycle that has yet to be competed 810. The duration of the therapeutic life cycle may also be modified by the clinician in real time, for example, the system controller 170 may be reconfigured by the clinician for an 8-day (192-hour) therapeutic life cycle.

The therapy algorithm 803 may use the balance and/or a change in the balance of the therapeutic life cycle in its analysis. For instance, it may be preferable to compete the therapeutic life cycle with a wide hysteresis control band rather than attempt to maintain a narrow hysteresis control band and fail to compete the therapeutic life cycle because the batteries have insufficient capacity to do so. The therapy algorithm 803 may be configured with this information and make its determination whether to switch to a narrow hysteresis control band or a wider hysteresis control band based upon, at least in part, the balance of the therapeutic life cycle or how much of the existing therapeutic life cycle it has yet to complete.

The therapy algorithm 803 may further read current battery charge level (BCL) as determined by the system controller 170 at 820. When the current battery charge level (BCL) is less than a first target charge level (TCL1) 836, which may indicate a low battery charge level in the system, the system controller 170 may be configured to select a wide hysteresis control band 860, alternatively when the current battery charge level (BCL) is greater than a second target battery charge level (TCL2) 832, which may indicate a high battery charge level in the system, the system controller 170 may be configured to select a narrow hysteresis control band 850. The first target charge level (TCL1) may be less than the second target charge level (TCL2) alternatively the first target battery charge level (TCL1) may be substantially equal to the second target battery charge level (TCL2). The battery charge level (BCL) may be determined using known electronic circuits.

In some embodiments, a low battery charge level may also indicate a high-leakage condition in the system and/or a high battery charge level may also indicate a low-leakage condition in the system. In some instances the therapy algorithm 803 may further determine whether the batteries have been replaced, the batteries have been recharged or an existing leak in the system has been addressed during the therapeutic life cycle.

In some embodiments, the system controller 170 may be configured to alternatively select the narrow hysteresis control band 850 when the battery charge level in the system is high or the wide hysteresis control band 860 when the battery charge level in the system is low.

In some embodiments, the TCL1 value and/or the TCL2 value may be based upon, at least in part, the balance of the therapeutic life cycle and may therefore be dynamic For example, as the balance of the therapeutic life cycle decreases with time so may the values of TCL1 and/or TCL2 decrease with time.

The therapy algorithm 803 may further the read the current flow rate (FR) of fluid between the pump and the porous pad as determined by the system controller 170 at 836. When the current flow rate (FR) is less than a first target flow rate (TFR1) 842, which may indicate a low-leakage condition in the system, the system controller 170 may be configured to select a narrow hysteresis control band 850, alternatively when the current flow rate (FR) is greater than a second target flow rate (TFR2) 840, which may indicate a high-leakage condition in the system, the system controller 170 may be configured to select a wide hysteresis control band 860. The first target flow rate (TFR1) may be less than the second target flow rate (TFR2) alternatively the first target flow rate (TFR1) may be substantially equal to the second target rate (TFR2). The current flow rate (FR) or leak rate may be inferred from the duty cycle of the pressure pump 112 and the duty cycle may be determined using know electronic circuits.

In some embodiments, the system controller 170 may be configured to alternatively select the narrow hysteresis control band 850 when the system is determined to be in a low-leak condition state or the wide hysteresis control band 860 if the system is determined to be in a high-leakage condition state. While, the alternative selection of either the narrow hysteresis control band 850 or wide hysteresis control band 860 has been discussed in the context of conserving battery power there may be other considerations. For example, the system controller 170 may be configured select a hysteresis control band with a tighter set of limits at the initiation of the therapeutic life cycle for the purpose of achieving and maintaining a therapeutic seal whilst the bonding agents of the dressing activates, after which the system may select a hysteresis control band with looser set of limits.

In some embodiments, the TFR1 value and/or the TFR2 value may be based upon, at least in part, the balance of the therapeutic life cycle and may therefore be dynamic. For example, as the balance of the therapeutic life cycle decreases with time so may the values of TFR1 and/or TFR2 decrease with time.

While the therapy algorithm 803 is described herein as having only a narrow hysteresis control band and wide hysteresis control band this is intended to be for illustration purposes only, as will be understood by a person having ordinary skill in the art, there may be more than two hysteresis control bands additionally/alternatively there may be one hysteresis control band and the size of the one or more hysteresis control band(s) may be dynamically varied based upon, at least in part, the balance of the therapeutic life cycle, the current battery charge level (BCL) and the current flow rate (FR).

In some embodiments, the balance of the therapeutic life cycle, the current battery charge level (BCL) and the current flow rate (FR) may be each be weighted and the therapy algorithm 803 may be configured to alternatively select the narrow hysteresis control band 850 or the wide hysteresis control band 860 based upon, at least in part, a determination of a weighted score.

Since, the therapy algorithm 803 utilizes a minimum wound site pressure (WPMin) it will have the added advantage of assisting the pressure pump 112 to restart against an existing system pressure. As stated above it is more difficult for the pressure pump 112 to restart against an existing system pressure and this may be exacerbated by a low battery charge level (BCL) and a corresponding decrease in battery terminal voltage. By utilizing a minimum wound site pressure (WPMin) this restriction may be eased because once the pressure pump 112 has gained momentum it may be able to then reach a higher maximum wound site pressure (WPMax), than it would otherwise have been able to with the current battery charge level (BCL)/battery terminal voltage.

In some embodiments, the therapy algorithm 803 may be a master algorithm, for example, if the system controller 170 includes both the PID controller and the bang-bang controller, i.e., a hybrid controller and/or a therapy algorithm 703 as described above any conflict between the two may be determined by the therapy algorithm 803. For example, while the therapy algorithm 703 may be configured to engage the bang-bang controller when the flow rate (FR) is less than or equal to the fixed target flow rate (TFR), but switch back to the PID controller when the flow rate (FR) is greater than the fixed target flow rate (TFR) this may be overridden by the therapy algorithm 803 based upon power consumption considerations rather than maintaining a target pressure (TP) in high leakage systems.

In some embodiments, the PID controller may be configured to have a hysteresis control band as described herein and the PID controller will send power to the DC motor 114 only when the wound site pressure (WP) has decayed to the minimum wound site pressure (WPMin) and the power to the DC motor 114 may also be decreased as it approaches the target pressure (TP). While the proposed therapy algorithm 803 has been described in terms of modifying and/or selecting 850, 860 hysteresis control bands its will be approached that it could equally have been described in terms of altering the minimum wound site pressure (WPMin), the maximum wound site pressure (WPMax), the differential wound site pressure range ($\delta$WP) or the differential pump pressure range ($\delta$PP) to maximize efficiency based upon, at least in part, the measurement of the power available, the leak into the system and the balance of the therapeutic life cycle.

While the illustrative embodiments are for a negative-pressure wound treatment system the system and methods described herein are applicable for other medical and non-medical systems where a pump is used and there would be a benefit to adjusting the control bands of the pump to improve system efficiency.

Further, while shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system comprising:
   a negative-pressure source including a pump adapted to generate a pump pressure (PP) and an electric motor for driving the pump in response to an application of power to the electric motor;
   a wound pressure sensor having an input for sensing a wound site pressure (WP) at a wound site and an output; and
   a system controller coupled to the electric motor and the output of the wound pressure sensor, the system controller configured to compare the wound site pressure (WP) to pressures within a hysteresis control band bounded by a maximum wound site pressure ($WP_{Max}$) and a minimum wound site pressure ($WP_{Min}$);
   wherein the maximum wound site pressure ($WP_{Max}$) and the minimum wound site pressure ($WP_{Min}$) are based upon a flow rate (FR) of fluid between the pump and the wound site and the system controller is further configured to maintain the wound site pressure (WP) within the hysteresis control band.

2. The system of claim 1, wherein the system controller includes an on-off controller adapted to reduce negative-pressure at the wound site if the wound site pressure (WP) is greater than the maximum wound site pressure ($WP_{Max}$) and increase negative pressure at the wound site if the wound site pressure (WP) is less than the minimum wound site pressure ($WP_{Min}$).

3. The system of claim 1, further comprising a pump pressure sensor having an input for sensing the pump pressure (PP) and an output providing a pump pressure signal to the system controller indicative of the pump pressure (PP).

4. The system of claim 1, wherein the system controller includes an on-off controller adapted to control negative-pressure at the wound site by reducing the power applied to the electric motor if the wound site pressure (WP) is greater than a maximum wound site pressure ($WP_{Max}$) and increasing the power applied to the electric motor if the wound site pressure (WP) is less than a minimum wound site pressure ($WP_{Min}$).

5. The system of claim 1, wherein the power applied to the electric motor is varied by varying a voltage applied to the electric motor.

6. The system of claim 5, wherein the system controller is further configured to determine the flow rate (FR) by determining a time rate of change of the voltage applied to the electric motor.

7. The system of claim 1, wherein the power applied to the electric motor is varied by varying a current drawn by the electric motor.

8. The system of claim 7, wherein the system controller is further configured to determine the flow rate (FR) by determining a time rate of change of the current drawn by the electric motor.

9. The system of claim 1, wherein the system controller is further configured to select a narrow hysteresis control band if the flow rate (FR) is less than a first target flow rate (TFR1) indicating a low-leak condition in the system.

10. The system of claim 9, wherein the system controller is further configured to select a wide hysteresis control band if the flow rate (FR) is greater than a second target flow rate (TFR2) indicating a high-leak condition in the system.

11. The system of claim 10, wherein the system controller is further configured to alternatively select the narrow hysteresis control band when the system is in a low-leakage condition or the wide hysteresis control band when the system is in a high-leakage condition.

12. The system of claim 10, wherein the first target flow rate (TFR1) is less than the second target flow rate (TFR2).

13. The system of claim 10, wherein the first target flow rate (TFR1) is substantially equal to the second target flow rate (TFR2).

14. The system of claim 1, wherein the power source is a battery, wherein the system for stimulating healing of tissue at the wound site is a portable system and the portable system is powered by the battery.

15. The system of claim 14, wherein the battery is a primary cell battery, wherein the primary cell battery is a non-rechargeable lithium battery.

16. The system of claim 14, wherein the battery is a secondary cell battery, wherein the secondary cell battery is a rechargeable lithium-ion battery.

17. The system of claim 14, wherein the system controller is further configured to determine a battery charge level (BCL).

18. The system of claim 17, wherein the system controller is further configured to select a wide hysteresis control band if the battery charge level (BCL) is less than a first target battery charge level (TCL1) indicating a low battery charge level in the system.

19. The system of claim 18, wherein the system controller is further configured to select a narrow hysteresis control band if the battery charge level (BCL) is greater than a second target battery charge level (TCL2) indicating a high battery charge level in the system.

20. The system of claim 19, wherein the first target battery charge level (TCL1) is less than the second target battery charge level (TCL2).

21. The system of claim 19, wherein the first target battery charge level (TCL1) is substantially equal to the second target battery charge level (TCL2).

22. The system of claim 19, wherein the system controller is further configured to alternatively select the narrow hysteresis control band when the battery charge level in the system is high or the wide hysteresis control band when the charge level in the system is low.

23. A method comprising:
  applying negative pressure to a dressing provided by a pump driven by an electric motor in response to an application of power to the electric motor;
  monitoring a wound pressure sensor having an input for sensing a wound site pressure (WP) and an output;
  determining a flow rate (FR) of fluid between the pump and the wound site;
  comparing the wound site pressure (WP) to pressures in a hysteresis control band bounded by a maximum wound site pressure ($WP_{Max}$) and a minimum wound site pressure ($WP_{Min}$) based upon the flow rate (FR); and
  maintaining the wound site pressure (WP) within the hysteresis control band.

24. The method of claim 23, further comprising reducing negative-pressure at the wound site if the wound site pressure (WP) is greater than the maximum wound site pressure ($WP_{Max}$) and increasing negative-pressure at the wound site if the wound site pressure (WP) is less than the minimum wound site pressure ($WP_{Min}$).

25. The method of claim 23, further comprising controlling negative pressure at the wound site by reducing the power applied to the electric motor if the wound site pressure (WP) is greater than a maximum wound site pressure ($WP_{Max}$) and increasing the power applied to the electric motor if the wound site pressure (WP) is less than a minimum wound site pressure ($WP_{Min}$).

26. The method of claim 23, wherein the flow rate (FR) is determined based upon a time rate of change of a voltage applied to the electric motor.

27. The method of claim 23, further comprising selecting a narrow hysteresis control band if the flow rate (FR) is less than a first target flow rate (TFR1) indicating a low-leak condition in the system.

28. The method of claim 27, further comprising selecting a wide hysteresis control band if the flow rate (FR) is greater than a second target flow rate (TFR2) indicating a high-leak condition in the system.

29. The method of claim 28, further comprising alternatively selecting the narrow hysteresis control band when the system is in a low-leakage condition or selecting the wide hysteresis control band when the system is in a high-leakage condition.

30. The method of claim 28, wherein the first target flow rate (TFR1) is less than the second target flow rate (TFR2).

31. The method of claim 28, wherein the first target flow rate (TFR1) is substantially equal to the second target flow rate (TFR2).

32. The method of claim 23, further comprising selecting a wide hysteresis control band if a battery charge level (BCL) is less than a first target battery charge level (TCL1) indicating a low battery charge level in the system.

33. The method of claim 32, further comprising selecting a narrow hysteresis control band if the battery charge level (BCL) is greater than a second target battery charge level (TCL2) indicating a high battery charge level in the system.

34. The method of claim 33, wherein the first target battery charge level (TCL1) is less than the second target battery charge level (TCL2).

35. The method of claim 33, wherein the first target battery charge level (TCL1) is substantially equal to the second target battery charge level (TCL2).

36. The method of claim 33, further comprising alternatively selecting the narrow hysteresis control band when the battery charge level in the system is high or selecting the wide hysteresis control band when the battery charge level (BCL) in the system is low.

37. A negative-pressure device comprising:
  a negative-pressure source having a pump and an electric motor for driving the pump in response to an application of power from a battery;
  a pressure sensor having an input for sensing a wound site pressure (WP) at a wound site and an output; and
  a system controller coupled to the electric motor and the pressure sensor and configured to determine a flow rate (FR) of fluid between the pump and the wound site and to maintain the wound site pressure (WP) within a hysteresis control band, wherein the hysteresis control band includes a range of pressures determined by the system controller in real time based upon a balance of the flow rate (FR) and a battery charge level (BCL) of the battery.

38. The system of claim 37, wherein the system controller is further configured to select a narrow hysteresis control band if the flow rate (FR) is less than a first target flow rate (TFR1) indicating a low-leak condition in the system.

39. The system of claim 38, wherein the system controller is further configured to select a wide hysteresis control band if the flow rate (FR) is greater than a second target flow rate (TFR2) indicating a high-leak condition in the system.

40. The system of claim 39, wherein the system controller is further configured to alternatively select the narrow hysteresis control band when the system is in a low-leakage condition or the wide hysteresis control band when the system is in a high-leakage condition.

* * * * *